United States Patent [19]
Sato et al.

[11] Patent Number: 5,459,045
[45] Date of Patent: Oct. 17, 1995

[54] REAGENT FOR IMMUNOASSAY, AND DEVICE USING THE SAME

[75] Inventors: Hiroshi Sato; Tadakazu Yamauchi, both of Saitama; Toshio Izako, Tokyo; Masahiro Nobuhara, Saitama; Ei Mochida, Tokyo, all of Japan

[73] Assignee: Mochida Pharmaceutical Co., Ltd., Tokyo, Japan

[21] Appl. No.: 149,917

[22] Filed: Nov. 10, 1993

Related U.S. Application Data

[62] Division of Ser. No. 480,165, Feb. 14, 1990, Pat. No. 5,283,176.

[30] Foreign Application Priority Data

Feb. 15, 1989 [JP] Japan ................................ 1-35815

[51] Int. Cl.⁶ .................................................. G01N 33/552
[52] U.S. Cl. .......................... 435/7.93; 436/527; 436/537; 436/817
[58] Field of Search .................... 435/7.93; 436/527, 436/537, 817

[56] References Cited

U.S. PATENT DOCUMENTS

| | | | |
|---|---|---|---|
| 4,585,741 | 4/1986 | Clevinger | 435/70.21 |
| 4,720,455 | 1/1988 | Babu et al. | 435/7.93 |
| 4,895,809 | 1/1990 | Schlabach et al. | 436/518 |

FOREIGN PATENT DOCUMENTS

| | | |
|---|---|---|
| 0088974 | 9/1983 | European Pat. Off. . |
| 538053 | 4/1993 | European Pat. Off. . |
| 62-151758 | 12/1985 | Japan . |
| 62-148857 | 12/1985 | Japan . |
| 2095831 | 10/1982 | United Kingdom . |
| 93/25672 | 12/1993 | WIPO . |

OTHER PUBLICATIONS

L. Tiefeneuer et al., J. Steroid Biochem., vol. 32, No. 2, pp. 251–257 (1989).
J. De Boever et al., Analytica Chimica Acta, vol. 170, pp. 117–123 (1985).
P. Luppa et al., Bioconjugate Chemistry, vol. 5, pp. 167–171 (1994).
Odell et al; Principles of Competitive Protein Binding Assay; Wiley & Sons 1983.

*Primary Examiner*—Mary E. Ceperley
*Attorney, Agent, or Firm*—Birch, Stewart, Kolasch & Birch

[57] ABSTRACT

A reagent for use in an immunoassay for measuring haptens, antigens or antibodies by means of a competitive binding method, which comprises a combination of an antibody and a labelled hapten or a labelled antigen or a combination of a hapten or an antigen and a labelled antibody, wherein the antibody and the labelled hapten or the labelled antigen in one combination or the hapten or the antigen and the labelled antibody in another combination are capable of undergoing reversible binding, and a device for use in an immunoassay wherein the reagent of the present invention is included in a single container.

An immunoassay can be performed in a short time by the use of the immunoassay device of the present invention.

14 Claims, 9 Drawing Sheets

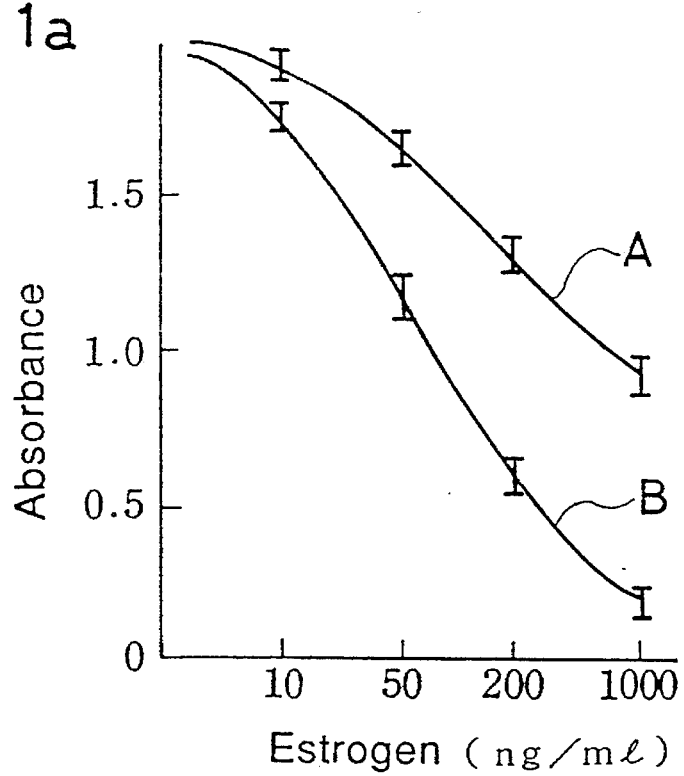
F I G. 1a
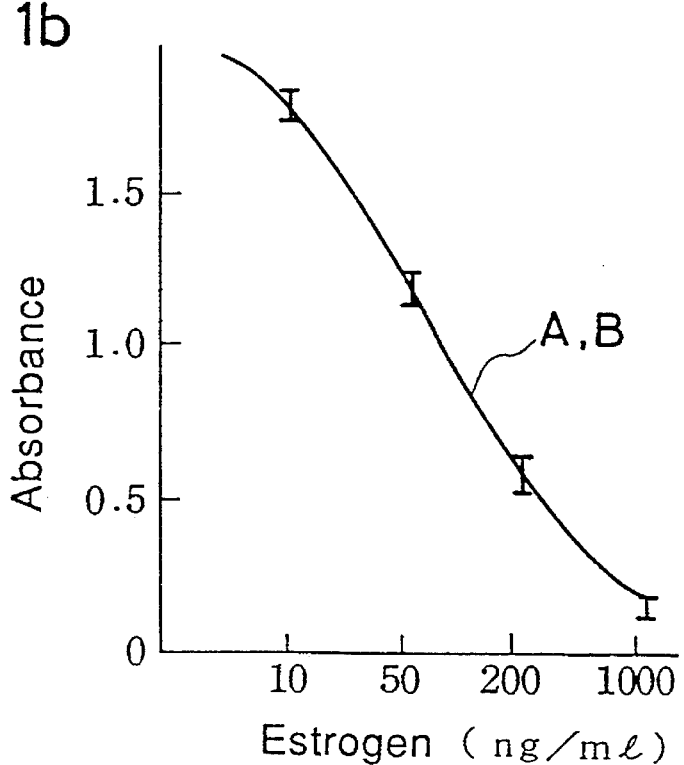
F I G. 1b

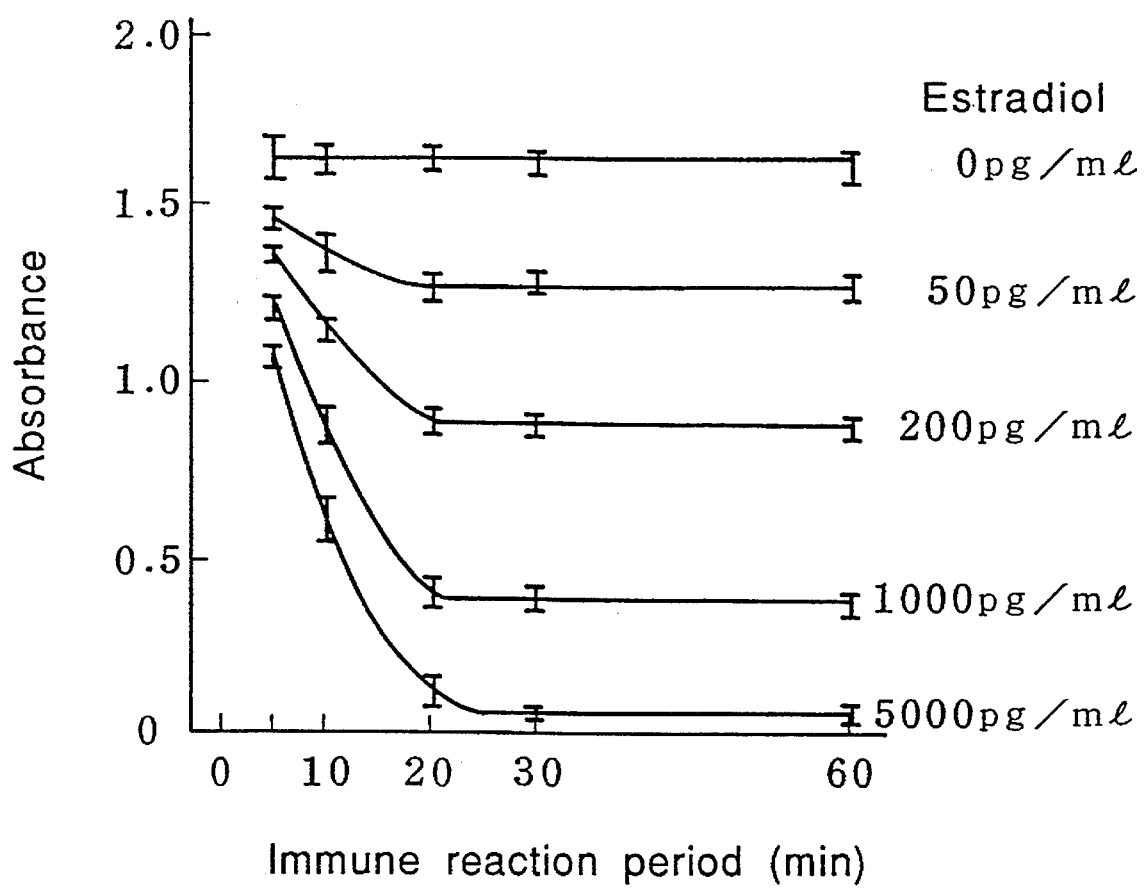
F I G.4

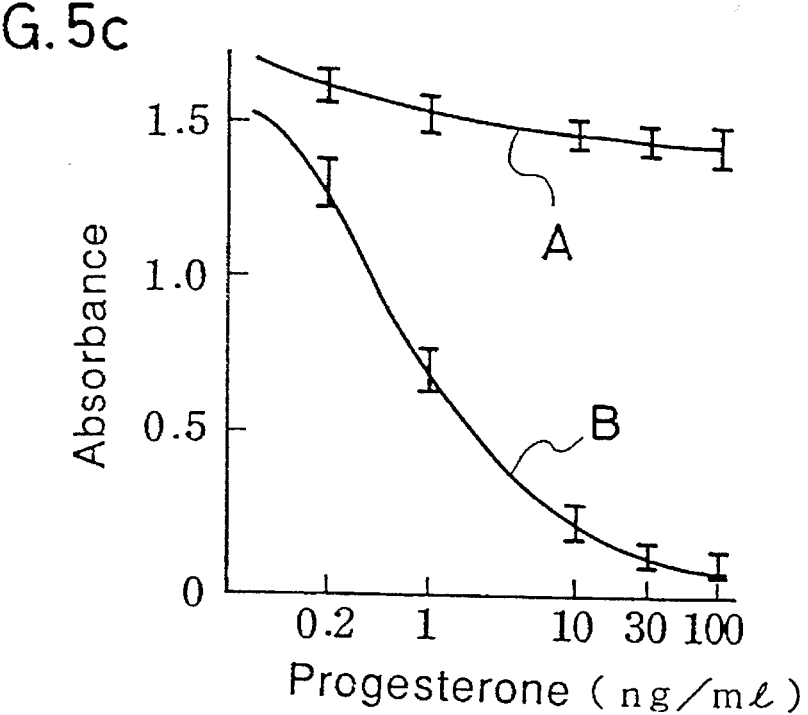
F I G. 5c
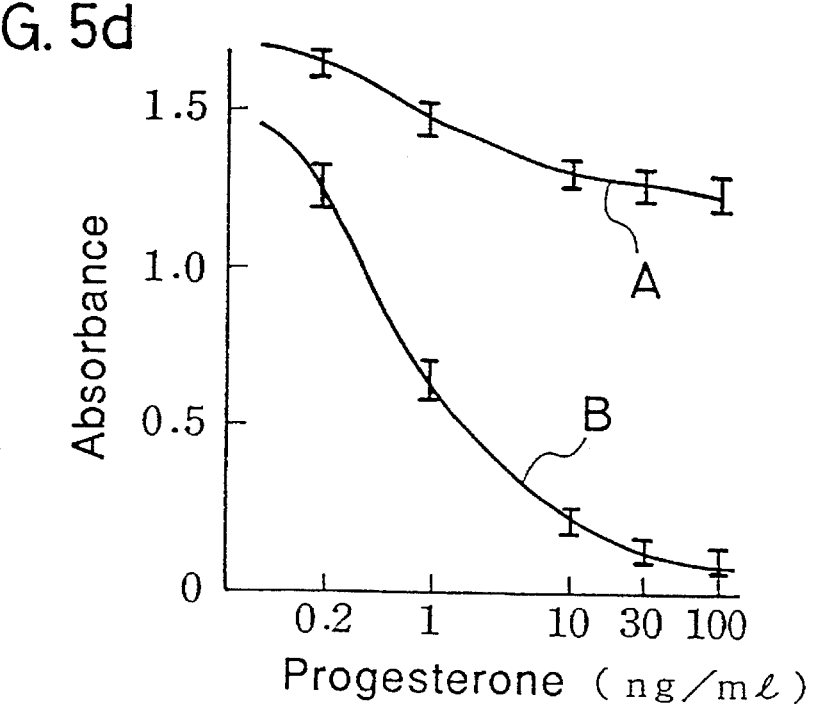
F I G. 5d

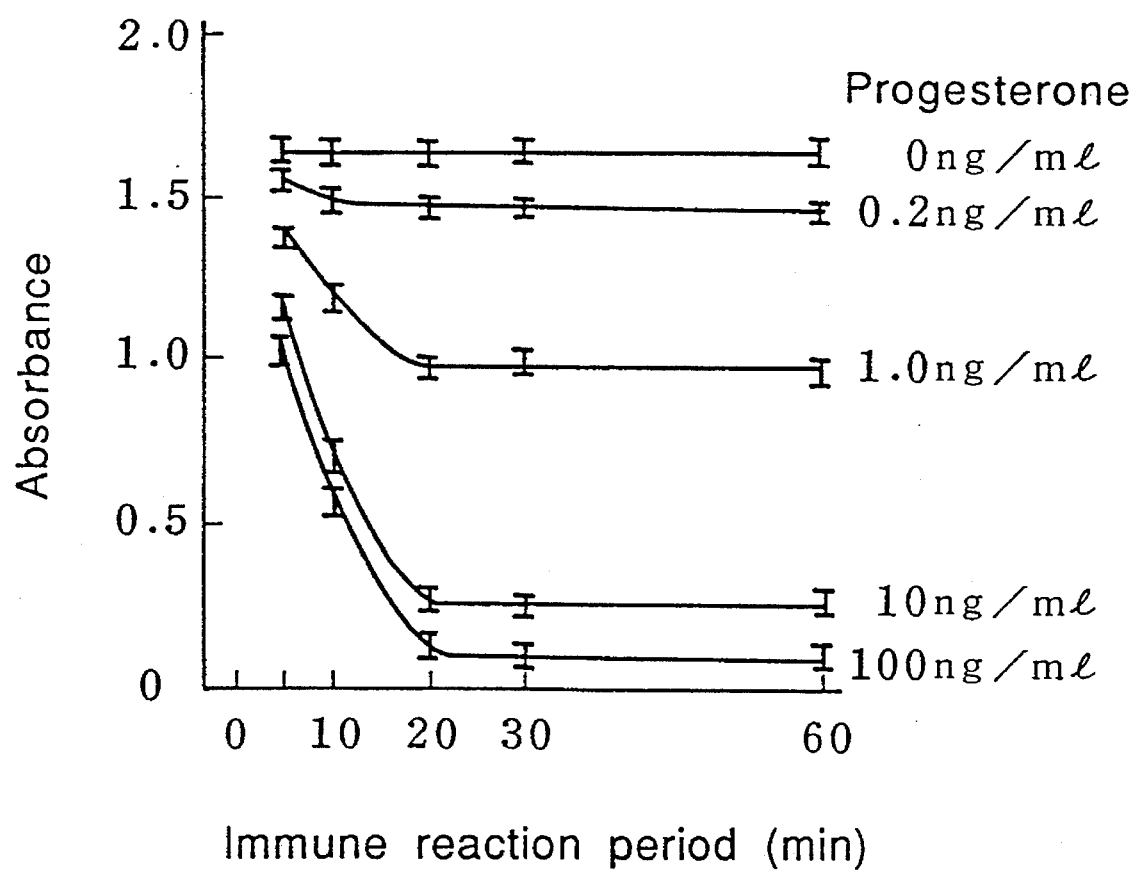
F I G. 6

REAGENT FOR IMMUNOASSAY, AND DEVICE USING THE SAME

This application is a divisional of application Ser. No. 07/480,165, filed on Feb. 14, 1990, now U.S. Pat. No. 5,283,176, the entire contents of which are hereby incorporated by reference.

BACKGROUND OF THE INVENTION

This invention relates to a reagent for use in an immunoassay and an immunoassay device in which the reagent is included in a container, for measuring haptens, antigens or antibodies by means of a competitive binding method.

Backed by the recent rapid progress in immunology and genetic engineering, various methods, as well as assay kits, for the measurement of trace substances in the body have been developed making use of immune reactions.

Such immune reaction-aided measurements are divided chiefly into a sandwich method and a competitive binding method on the basis of the measuring principles.

A principle of the sandwich method, in the case of an antigen as a substance to be detected for example, is to capture the antigen by holding (sandwiching) it between an antibody (insoluble antibody) which has a specific affinity for one of the antigenicity-active sites (determinant group) of the antigen molecule and another antibody (labelled antibody) which also has a specific affinity but for another determinant group of the antigen molecule and then to measure the quantity of the antigen in the sample based on the signals originating from the labelled antibody. In consequence, the test substance has to be an antigen which has at least two specific determinant groups.

Many studies have been performed on the sandwich method, which is generally used for the measurement of high molecular weight substances, such as proteins, polypeptides, saccharides, lipids and their complexes. For example, since the reagent for use in the measurement of antigens comprises an insoluble antibody and another labelled antibody, and these insoluble and labelled antibodies do not react with each other if present together, an assay kit in which both of these antibodies are previously included in a single container has been developed (Japanese Patent Public Disclosure No. 57-136165). In addition, making use of this assay kit, an easily operable automatic measuring device in which an immune reaction can be started by simply adding a test sample into a container has been developed.

In the convenient competitive binding method, in the case of an antigen as a substance to be detected for example, the antigen in a sample and a labelled antigen are competitively bound to an antibody, and the quantity of the antigen in the sample is then measured based on the signals originating from the labelled antigen. In consequence, the substance to be tested may be either an antigenic substance having only one determinant group or an antibody prepared from such an antigenic substance, or a hapten and an antibody which is prepared by using an immunogenic compound composed of a hapten and an immunoactive carrier.

The competitive binding method is generally used for the measurement of substances which are difficult to be analyz by the sandwich technique, for example, substances having relatively low molecular weights, such as steroids, amines, amino acids and peptides.

In the convenient competitive binding method, however, the antigen-antibody reaction is irreversible. Therefore, in the case of an antigen as a substance to be detected for example, accurate measurement can be achieved when a labelled antigen is added into a container, in which an insoluble antibody is previously included, only after, or at the same time as, the addition of a sample into the container. In consequence, it has been generally considered that an insoluble antibody and a labelled antigen for use in an immune reaction could not be included together in one container prior to the addition of a sample.

As described above, the competitive binding method is a useful technique for the measurement of trace substances having relatively low molecular weights. However, complex operations are required in the case of manual measurement, because an insoluble antibody and a labelled antigen for use in an immune reaction have to be included in separate containers, and the labelled antigen held in the separate container has to be injected only after, or at the same time as, the addition of a sample into the container in which the insoluble antibody is previously included. In addition, a system for keeping and injecting a labelled antigen for every measuring item is required in the case of an automatic measuring device, which has been an obstacle to the development of an automatic device for the measurement of multiple items.

For the purpose of solving such a problem, a method for including both an insoluble antibody and a labelled antigen in a single container making use of a freeze-drying technique has been proposed (Japanese Patent Public Disclosure No. 62-148857 and Japanese Patent Public Disclosure No. 62-151758). However, these prior patents do not disclose stabilities of the insoluble antibody and labelled antigen with the passage of time when the method is applied to practical operation. Therefore, a problem of stabilities with the passage of time still remains unsolved.

SUMMARY OF THE INVENTION

In view of the above, it therefore is an object of the present invention to provide an immunoassay reagent making use of the principle of the competitive binding method, which comprises a combination of a reversibly bindable insoluble antibody and a labelled hapten, a combination of a reversibly bindable insoluble antibody and a labelled antigen, a combination of a reversibly bindable insoluble hapten and a labelled antibody, or a combination of a reversibly bindable insoluble antigen and a labelled antibody.

Another object of the present invention is to provide a device for use in an immunoassay wherein any one of the above-described immunoassay reagents is included in a single container.

In one form of the present invention, there is provided a reagent for use in an immunoassay for measuring a hapten, comprising (a) a labelled hapten comprising a first hapten and a labelling agent bound to said first hapten, and (b) an antibody prepared by using an immunogen comprising a second hapten and an immunoactive carrier bound to said second hapten, wherein said first and second haptens are individually selected from the group consisting of the hapten to be measured and derivatives thereof, and said labelled hapten (a) and said antibody (b) are capable of undergoing reversible binding; or a reagent for use in an immunoassay for measuring a hapten, comprising (c) a first hapten, and (d) a labelled antibody comprising an antibody (b) prepared by using an immunogen comprising a second hapten and an immunoactive carrier bound to said second hapten, and a labelling agent bound to said antibody, wherein said first and second haptens are individually selected from the group consisting of the hapten to be measured and derivatives thereof, and said first hapten (c) and said labelled antibody (d) are capable of undergoing reversible binding.

In a second form of the present invention, there is provided a reagent for use in an immunoassay for measuring an antigen, comprising (e) a labelled antigen comprising a first antigen and a labelling agent bound to said first antigen, and (f) an antibody prepared by using an immunogen of second antigen, wherein said first and second antigens are individually selected from the group consisting of the antigen to be measured and derivatives thereof, and said labelled antigen (e) and said antibody (f) are capable of undergoing reversible binding; or a reagent for use in an immunoassay for measuring an antigen, comprising (g) a first antigen, and (h) a labelled antibody comprising an antibody (f) prepared by using an immunogen of a second antigen, and a labelling agent bound to said antibody, wherein said first and second antigens are individually selected from the group consisting of the antigen to be measured and derivatives thereof, and said first antigen (g) and said labelled antibody (h) are capable of undergoing reversible binding.

In a third form of the present invention, there is provided a reagent for use in an immunoassay for measuring an antibody, comprising (a) a labelled hapten comprising a first hapten and a labelling agent bound to said first hapten, and (b) an antibody prepared by using an immunogen comprising a second hapten and an immunoactive carrier bound to said second hapten, wherein said first and second haptens are individually selected from the group consisting of the hapten to be measured and derivatives thereof, and said labelled hapten (a) and said antibody (b) are capable of undergoing reversible binding; or a reagent for use in an immunoassay for measuring an antibody, comprising (c) a first hapten, and (d) a labelled antibody comprising an antibody (b) prepared by using an immunogen comprising a second hapten and an immunoactive carrier bound to said second hapten, and a labelling agent bound to said antibody, wherein said first and second haptens are individually selected from the group consisting of the hapten to be measured and derivatives thereof, and said first hapten (c) and said labelled antibody (d) are capable of undergoing reversible binding.

In a fourth form of the present invention, there is provided a reagent for use in an immunoassay for measuring an antibody, comprising (e) a labelled antigen comprising a first antigen and a labelling agent bound to said first antigen, and (f) an antibody prepared by using an immunogen of second antigen, wherein said first and second antigens are individually selected from the group consisting of the antigen to be measured and derivatives thereof, and said labelled antigen (e) and said antibody (f) are capable of undergoing reversible binding; or a reagent for use in an immunoassay for measuring an antibody, comprising (g) a first antigen, and (h) a labelled antibody comprising an antibody (f) prepared by using an immunogen of a second antigen, and a labelling agent bound to said antibody, wherein said first and second antigens are individually selected from the group consisting of the antigen to be measured and derivatives thereof, and said first antigen (g) and said labelled antibody (h) are capable of undergoing reversible binding.

In a fifth form of the present invention, there is provided a device for use in an immunoassay wherein any one of the above-described immunoassay reagents is included in a single container.

The term "hapten" as used herein refers to any commonly called "incomplete antigen" which is inactive itself as an immunogen regardless of the presence of a determinant group, but becomes active when it is linked to an immunoactive carrier. Also, the term "antigen" as used herein refers to any commonly called "complete antigen" which is active as an immunogen as it is.

Other objects and advantages of the present invention will be made apparent by the following description.

BRIEF DESCRIPTION OF THE DRAWINGS

FIGS. 1a, 1b, 1c and 1d are graphs showing results of a study on the existence of reversible immune reaction between anti-estrogen antibodies and labelled estrogen derivatives.

FIG. 4 is a graph showing results of a study on the reaction time required for the completion of equilibrium state in the immune reaction for the measurement of estradiol.

FIGS. 5a, 5b, 5c and 5d are graphs showing results of a study on the existence of reversible immune reaction between anti-progesterone antibodies and labelled progesterone derivatives.

FIG. 6 is a graph showing results of a study on the reaction time required for the completion of equilibrium state in the immune reaction for the measurement of progesterone.

DETAILED DESCRIPTION OF THE INVENTION

Figure 1C:
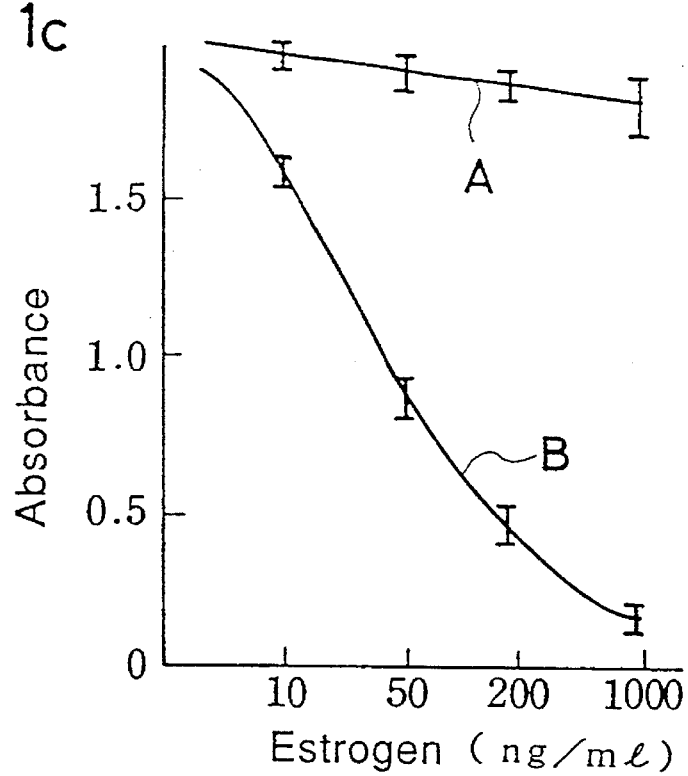
Figure 1D:
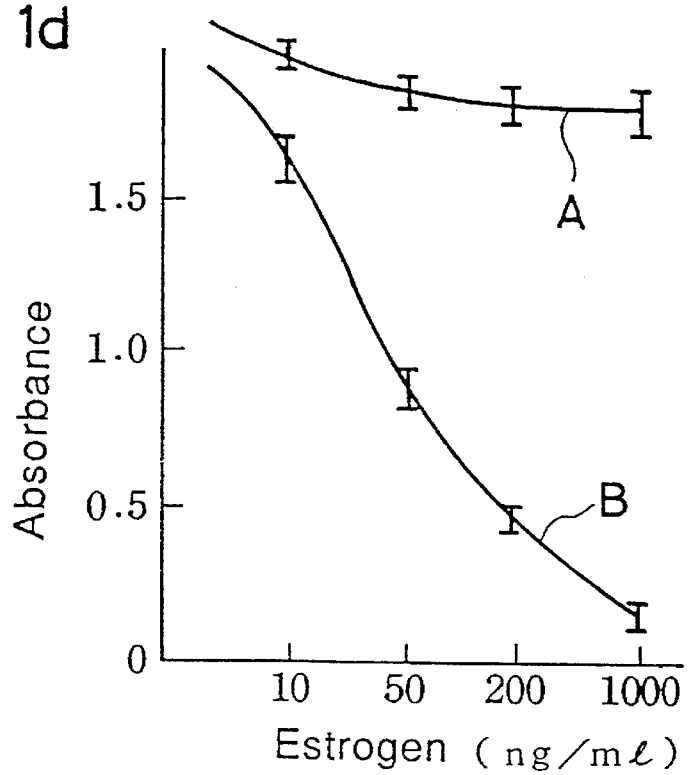

Any immunoassay of the prior art is performed based on the assumption that an immune reaction proceeds in the direction of the formation of antigen-antibody complexes and the reaction is almost irreversible.

However, the inventors of the present invention have predicted that, if a combination of an antibody and a hapten is used in which the immune reaction reaches its equilibrium state quickly and binding of the antibody and the hapten is reversible, a new competitive binding method could be established making use of the principle of the commonly used competitive binding method. In such a new competitive binding method, a combination of an insoluble antibody and a labelled hapten or a combination of an insoluble hapten and a labelled antibody, for use in an intended immune reaction for the immunoassay of haptens, may be included previously in a single container. Such a new competitive binding method may also be usable even when an immune reaction occurs between the antibody and the hapten during the preservation period, because, due to the reversible nature of the reaction, the labelled hapten molecules once bound to the insoluble antibody molecules or the labelled antibody molecules once bound to the insoluble hapten molecules will be unbound again in proportion to the amount of hapten molecules in a sample newly injected into the container and, instead, the hapten molecules in the sample will bind to the antibody molecules.

In the same manner, the inventors of the present invention have predicted that, if a combination of an antibody and a hapten or an antigen is used in which the immune reaction reaches its equilibrium state quickly and binding of the antibody and the hapten or the antigen is reversible, a new competitive binding method could be established making use of the principle of the commonly used competitive binding method. In such a new competitive binding method, a combination of an insoluble hapten or an insoluble antigen and a labelled antibody or another combination of an insoluble antibody and a labelled hapten or a labelled antigen, for use in an intended immune reaction for the immunoassay of antigens or antibodies, may be included previously in a single container. Such a new competitive binding method may also be usable even when an immune reaction occurs between the insoluble antibody and the labelled hapten or the labelled antigen or between the insoluble hapten or insoluble antigen and the labelled antibody during the preservation period, because, due to the reversible nature of the reaction, the labelled antigen molecules once bound to the insoluble antibody molecules or the labelled antibody molecules once bound to the insoluble antigen molecules will be unbound again in proportion to the amount of antigen molecules in a sample newly injected into the container and, instead, the antigen molecules in the sample will bind to the antibody molecules, or the labelled antibody molecules once bound to the insoluble hapten molecules or the antigen molecules (or the labelled hapten molecules or the labelled antigen molecules once bound to the insoluble antibody molecules) will be unbound again in proportion to the amount of antibody molecules in a sample newly injected into the container and, instead, the antibody molecules in the sample will bind to the hapten molecules or the antigen molecules.

The present invention has been accomplished by finding such combinations of antibodies and haptens or antibodies and antigens in which the immune reaction proceeds reversibly and reaches its equilibrium state quickly.

The immunoassay reagent of the present invention is useful for the measurement of specific substances, such as haptens, antigens and antibodies, in a sample by means of a competitive binding method.

The measuring principle is described below, firstly taking the case of a hapten as an example of the substance to be measured.

When a substance to be measured is a hapten, the reagent of the present invention is divided into two cases: "case 1" being a combination of a labelled hapten (a) comprising a first hapten and a labelling agent bound to said first hapten and an antibody (b) prepared by using an immunogen comprising a second hapten and an immunoactive carrier bound to said second hapten; and "case 2" being a combination of a first hapten (c) and a labelled antibody (d) comprising an antibody (b) prepared by using an immunogen comprising a second hapten and an an immunoactive carrier bound to said second hapten and a labelling agent bound to said antibody.

In the "case 1", since the antibody (b) and the labelled hapten (a) in the reagent are capable of undergoing reversible binding, a hapten in a sample to be measured and the labelled hapten (a) in the reagent bind competitively to the antibody (b) in the reagent. In a device for use in an immunoassay according to the present invention, wherein such a reagent is included in a single container, a hapten in a sample to be measured and the labelled hapten (a) bind competitively to the antibody (b) which is included in the container in an insolubilized form.

In the "case 2", since the hapten (c) and the labelled antibody (d) in the reagent are capable of undergoing reversible binding, a hapten in a sample to be measured and the hapten (c) in the reagent bind competitively to the labelled antibody (d) in the reagent. In a device for use in an immunoassay according to the present invention, wherein such a reagent is included in a single container, a hapten in a sample to be measured and the hapten (c) which is included in the container in an insolubilized form bind competitively to the labelled antibody (d).

In either case, the amount of a hapten in a sample is measured by detecting signals originating from a labelled insoluble substance after B/F separation (B, bound form; F, free form).

When a substance to be measured is an antigen, the measuring principle is the same as in the case of a hapten as described above, except that an immunoactive carrier is not necessary, and also provided that the term "hapten" in the description is replaced by another term "antigen". The principle in the case of the measurement of a compound comprising a hapten and an immunoactive carrier or an antibody prepared by using an antigen as the immunogen can be explained in the same manner.

Briefly, the measuring device of the present invention is divided into two cases: a case in which a hapten (or an antigen) is included in a container in an insolubilized form, and an antibody in a sample and a labelled antibody bind competitively to the insoluble hapten (or antigen); and the other case in which an antibody is included in a container in an insolubilized form, and the insoluble antibody and an antibody in a sample bind competitively to a labelled hapten (or a labelled antigen comprising an antigen and a labelling agent).

In either case, the amount of an antibody in a sample is measured by detecting signals originating from a labelled insoluble substance after B/F separation.

Thus, the principle of the immunoassay making use of the immunoassay reagent of the present invention is explained hereinabove.

Next, a combination of a labelled hapten (a) and an antibody (b) and another combination of a labelled antigen and an antibody are explained, which are applied to the reagent of the present invention for use in such immunoassays.

It is preferred that first hapten of the labelled hapten (a) and the second hapten (which is used after binding it to an immunoactive carrier) used as the immunogen for the preparation of the antibody (b) are analogous but different from each other, having different chemical structures, respectively. Since the binding ability between the labelled hapten (a) and the antibody (b) varies widely by the use of such analogous substances, a combination of a member of the group of the labelled hapten (a) and a member of the group of the antibody (b), which are capable of undergoing reversible binding, can be selected. In other words, the reaction between the labelled hapten (a) and the antibody (b) becomes reversible, if a hapten, whose chemical structure is analogous to but different from the second hapten used as the immunogen for the preparation of the antibody (b) and whose cross-reaction ability with the antibody is relatively small, is labelled and used as the labelled hapten (a). However, even if a first hapten for use in the labelled hapten (a) and a second hapten to be used as the immunogen for the preparation of the antibody (b) have the same chemical structure, these haptens may also be applicable, because the labelled hapten (a) and the antibody (b) prepared by using these first and second haptens having the same chemical structure are sometimes capable of undergoing reversible binding.

In a practical immunoassay, a substance to be measured becomes a third factor of the chemical structures. In general, when the substance to be measured is a hapten, the second hapten used as the immunogen for the preparation of the antibody (b) may have the same chemical structure as that of the hapten to be measured or have a slightly modified chemical structure of the hapten to be measured but having the same antigenicity, and an immunoactive carrier is linked to a site of the second hapten where the antigenicity of the second hapten may not be changed.

A labelled hapten, on the other hand, may be obtained by labelling a substance (hapten) having a certain chemical structure which has an affinity to a prepared antibody (b) and is capable of undergoing reversible binding to the antibody (b).

When the substance to be measured is an antibody which is made against an immunogen comprising a hapten and an immunoactive carrier, it is preferred that a first hapten having the same chemical structure as that of the hapten which is used in the immunogen for the preparation of the antibody to be measured or having a slightly modified chemical structure of the hapten in the immunogen but having the same antigenicity be used for the preparation of the labelled hapten (a), and a second hapten having a slightly different chemical structure from that of the hapten used in the immunogen for the preparation of the antibody to be measured be bound to an immunoactive carrier and used as the immunogen for use in the preparation of the antibody (b).

When the substance to be measured is an antigen or an antibody which is made against an antigen, conditions for the selection of the chemical structure of the first and second haptens are the same as those in the case of the above-described substances to be measured (a hapten and an antibody which is made against an immunogen comprising a hapten and an immunoactive carrier), except that immunoactive carriers are not required.

The following explains a combination of a labelled antibody (d) and a hapten (c) and another combination of a labelled antibody and an antigen, which are applied to the reagent of the present invention.

It is preferred that a first hapten (c) for use in the immunoassay reagent of the present invention and a second hapten (which is used after binding it to an immunoactive carrier) used as the immunogen for the preparation of the labelled antibody (d) are analogous but different from each other having different chemical structures, respectively. Since the binding ability between the hapten (c) and the labelled antibody (d) varies widely by the use of such analogous substances, a combination of a member of the group of the hapten (c) and a member of the group of the labelled antibody (d), which are capable of undergoing reversible binding, can be selected. However, even if a first hapten (c) for use in the immunoassay reagent of the present invention and a second hapten to be used as the immunogen for the preparation of the labelled antibody (d) have the same chemical structure, these haptens may also be applicable, because the hapten (c) and the labelled antibody (d) prepared by using these first and second haptens having the same chemical structure are sometimes capable of undergoing reversible binding.

In general, when the substance to be measured is an antibody which is made against an immunogen comprising a hapten and an immunoactive carrier, a first hapten having the same chemical structure as that of the hapten which is used in the immunogen for the preparation of the antibody to be measured or having a slightly modified chemical structure of the hapten in the immunogen but having the same antigenicity is used for the preparation of the hapten (c), and a second hapten having a slightly modified chemical structure from that of the hapten used in the immunogen for the preparation of the antibody to be measured is bound to an immunoactive carrier and used as the immunogen for use in the preparation of the labelled antibody (d), because chemical structures of the first and second haptens are such that the hapten (c) for use in the immunoassay reagent of the present invention and the labelled antibody (d) become capable of undergoing reversible binding.

When the substance to be measured is a hapten, the second hapten used as the immunogen for the preparation of the labelled antibody (d) may have the same chemical structure as that of the hapten to be measured or have a slightly modified chemical structure of the hapten to be measured but having the same antigenicity, and an immunoactive carrier is linked to a site of the second hapten where the antigenicity of the second hapten may not be changed. The hapten (c) for use in the immunoassay reagent of the present invention, on the other hand, may be obtained by selecting a certain chemical structure which has an affinity to a labelled antibody (d) and is capable of undergoing reversible binding to the labelled antibody (d).

When the substance to be measured is an antigen, or the immunogen for use in the preparation of an antibody to be measured is not a hapten but an antigen, conditions for the selection of the chemical structure of the first and second haptens are the same as those in the above description wherein a substance to be measured or an immunogen for use in the preparation of an antibody to be measured is a hapten, except that immunoactive carriers are not required.

The term "modified chemical structure" or the like as used hereinabove is intended to include any derivative which can be prepared by using commonly used techniques.

Principles of the combination of a labelled hapten or a labelled antigen and an antibody and another combination of a hapten or an antigen and a labelled antibody, which are used in the measuring device of the present invention, are explained above. The following concretely describes the example of samples which can be detected and measured by using the immunoassay reagent or the immunoassay device of the present invention, and substances for use in the immunoassay reagent of the present invention for measuring these test samples.

The immunoassay reagent or the immunoassay device of the present invention can be used for the measurement of substances having relatively low molecular weights, which are called haptens, such as: steroids, which comprises estrogens including estrone, estradiol and estriol, gestagens including progesterone, androgens including testosterone, mineral corticoids including aldosterone, and glucocorticoids including corticosterone; thyroid hormones, including thyroxine; amino acids and amines; drugs, including digoxin; and peptides, including angiotensin and α-hANP; as well as metabolites of these substances.

The immunoassay reagent or the immunoassay device of the present invention can also be used for the measurement of antigens, such as luteinizing hormone (LH), thyroid-stimulating hormone (TSH), human chronic gonadotropin (hCG) and carcinoembryonic antigen (CEA), as well as metabolites thereof.

Still more, the immunoassay reagent or the immunoassay device of the present invention can be used for the measurement of antibodies which are made in the body against immunogens, such as hepatitis B virus, rubella virus and various allergens.

The immunoassay reagent or the immunoassay device of the present invention is useful especially for the measurement of haptens, more especially for the measurement of estrogens and their metabolites and gestagens and their metabolites. The following exemplifies the combination of antibodies and labelled haptens for use in the immunoassay reagent and the immunoassay device of the present invention for the measurement of urinary estrogen, blood estradiol or blood progesterone.

For the measurement of urinary estrogen or blood estradiol using the immunoassay reagent or the immunoassay device of the present invention, it is preferred to use a labelled hapten (a) in which a first hapten for the preparation of the labelled hapten (a) is selected from the group consisting of compounds represented by the following formulae I to IV and an antibody (b) which is prepared by using an immunogen comprising a second hapten selected from the group consisting of compounds represented by the following formulae I to IV and an immunoactive carrier bound to the second hapten:

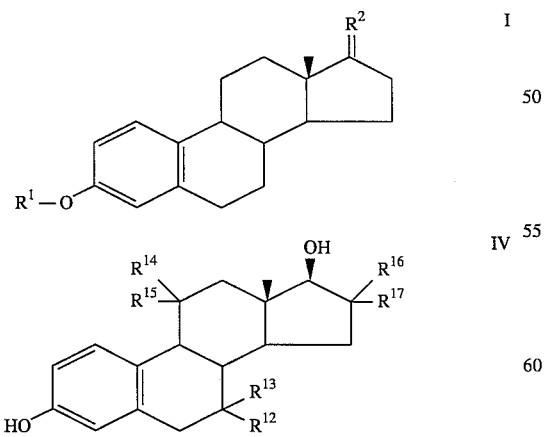

wherein $R^1$ is hydrogen, and $R^2$ is $Y^1$—Z; or $R^1$ is $Y^2$—Z and $R^2$ is oxygen;

wherein $Y^1$ is a straight-chain, branched, or cyclic radical intervening Z and the steroid nucleus comprising a backbone having 1 to 10 carbon atoms and/or hetero atoms, bonded to the steroid nucleus by a double bond; $Y^2$ is a straight-chain, branched, or cyclic radical intervening Z and the oxygen comprising a backbone having 0 to 10 carbon atoms and/or hetero atoms bonded to the oxygen by a single bond; and Z is a radical selected from the group consisting of hydrogen, —$NH_2$, —SH, —COOH, —CHO and

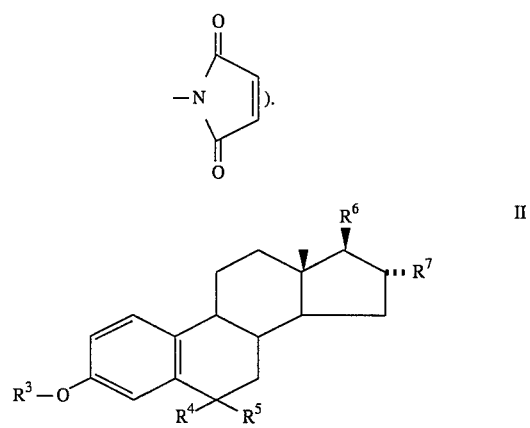

wherein $R^3$, $R^4$ and $R^5$ are hydrogen, one of $R^6$ and $R^7$ is hydrogen, and the other is $Y^3$—Z; $R^3$ is $Y^2$—Z, $R^4$, $R^5$ and $R^7$ are hydrogen, and $R^6$ is $Y^3$—Z; $R^3$ and $R^7$ are hydrogen, one of $R^4$ and $R^5$ is hydrogen and the other is $Y^3$—Z, and $R^6$ is hydroxyl; or $R^3$ and $R^7$ are hydrogen, $R^4$ and $R^5$ together represent $Y^1$—Z bonded to the steroid nucleus by a double bond, and $R^6$ is hydroxyl;

wherein $Y^1$ is a straight-chain, branched, or cyclic radical intervening Z and the steroid nucleus comprising a backbone having 1 to 10 carbon atoms and/or hetero atoms, bonded to the steroid nucleus by a double bond; $Y^2$ is a straight-chain, branched, or cyclic radical intervening Z and the oxygen comprising a backbone having 0 to 10 carbon atoms and/or hetero atoms bonded to the oxygen by a single bond; $Y^3$ is a straight-chain, branched, or cyclic radical intervening Z and the steroid nucleus comprising a backbone having 1 to 10 carbon atoms and/or hetero atoms, bonded to the steroid nucleus by a single bond; and Z is a radical selected from the group consisting of hydrogen, —$NH_2$, —SH, —COOH, —CHO and

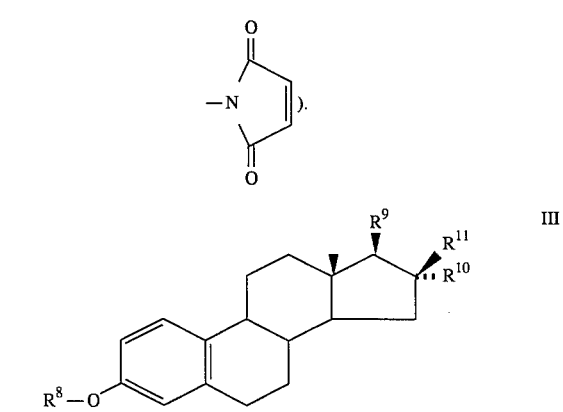

wherein $R^8$ is hydrogen, $R^9$ is $Y^3$—Z and one of $R^{10}$ and $R^{11}$ is $Y^3$—Z, and the other is hydrogen; $R^8$ is hydrogen, one of $R^9$ and $R^{10}$ is hydroxyl and the other is $Y^3$—Z, and $R^{11}$ is hydrogen; or $R^8$ is $Y^2$—Z, $R^9$ is $Y^3$—Z, $R^{10}$ is $Y^4$—Z, and $R^{11}$ is hydrogen; and wherein $Y^2$ is a straight-chain, branched, or cyclic radical intervening Z and the oxygen comprising a backbone having 0 to 10 carbon atoms and/or hetero atoms bonded to the oxygen by a single bond; $Y^3$ and $Y^4$ are individually a straight-chain, branched, or cyclic radical intervening Z and the steroid nucleus comprising a backbone having 1 to 10 carbon atoms and/or hetero atoms, bonded to the steroid nucleus by a single bond; and Z is a radical selected from the group consisting of hydrogen, —$NH_2$, —SH, —COOH, —CHO and

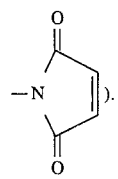

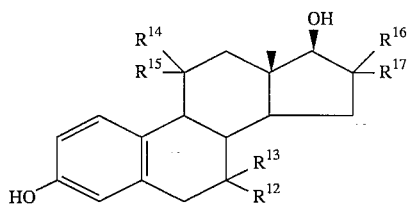

IV wherein one of $R^{12}$, $R^{13}$, $R^{14}$, $R^{15}$, $R^{16}$ and $R^{17}$ is $Y^3$—Z and the others are hydrogen; or $R^{12}$ and $R^{13}$, $R^{14}$ and $R^{15}$, or $R^{16}$ and $R^{17}$ together represent $Y^1$—Z bonded to the steroid nucleus by a double bond, and the others are hydrogen; wherein $Y^1$ is a straight-chain, branched, or cyclic radical intervening Z and the steroid nucleus comprising a backbone having 1 to 10 carbon atoms and/or hereto atoms, bonded to the steroid nucleus by a double bond; $Y^3$ is a straight-chain, branched, or cyclic radical intervening Z and the steroid nucleus comprising a backbone having 1 to 10 carbon atoms and/or hereto atoms, bonded to the steroid nucleus by a single bond; and Z is a radical selected from the group consisting of hydrogen, —$NH_2$, —SH, —COOH, —CHO and

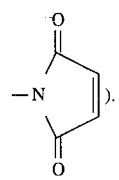

Examples of the compounds represented by the formulae I to IV are listed below.

The compound corresponding to the formula I includes estrone, estrone-17-carboxymethyl oxime and estrone-3-carboxymethyl ether. The compound corresponding to the formula II includes estradiol, estradiol-3-carboxymethyl ether, estradiol-6α-hemisuccinate, estradiol-6-carboxymethyl oxime, estradiol-17α-hemisuccinate and estradiol-17β-hemisuccinate. The compound corresponding to the formula III includes estriol, estriol-3-carboxymethyl ether, estriol-16α, 17 β-dihemisuccinate, estriol-16β, 17β-dihemisuccinate, estriol-16α-glucuronide and estriol-17β-glucuronide. The compound corresponding to the formula IV comprises estradiol-7-hemisuccinate, estradiol-7-carboxyethyl thioether, estradiol-11-hemisuccinate and estradiol-16α-hemisuccinate.

The following describes preparation methods and combinations of antibodies and labelled haptens for use in the immunoassay reagent and the immunoassay device of the present invention for measuring urinary estrogen.

Measurement of urinary estrogen is usually applied to a monitor system of the fetoplacental unit function in pregnant women, because conditions of the fetoplacental unit in a pregnant woman can be evaluated by measuring the amount of estriol which is produced in the fetoplacental unit and excreted into urine of the pregnant woman.

The major component of urinary estrogen comprises estriol derivatives, and estriol-16α-glucuronide is the most important derivative among them. For the measurement of urinary estrogen, therefore, it is desirable to use an antibody to estriol-16α-glucuronide as the main substance to be measured, which is cross-reactive to other coexisting conjugated estriols, conjugated estradiols and conjugated estrones in the sample.

Such an antibody may be obtained by immunizing an animal with an immunogen which comprises an immunoactive carrier and an estriol derivative, an estradiol derivative or an estrone derivative and then preparing a hybridoma which produces an anti-estrogen antibody by means of a cell fusion technique.

Since the main component of urinary estrogen is a conjugated estriol, the use of an estriol derivative, rather than an estrone derivative, is effective as a hapten of the immunogen which is used for the preparation of an antibody for use in the measurement of urinary estrogen.

Antibodies thus prepared are then checked for their cross-reactivities and measurable ranges of estrogen, in order to select an antibody which shows about 100 ng/ml of the 50%-inhibition concentration of estriol-16α-glucuronide, estimated from a standard curve, and has cross-reactivities to estriol, estradiol, estrone, conjugated estriol at the 17-position, conjugated estriol at the 16-position, conjugated estriol at the 16- and 17-positions, conjugated estradiol at the 17-position, and the like.

Preparation of a labelled estrogen is performed by selecting an estrogen derivative whose binding ability to the antibody is slightly lower than or similar to that of the estrogen to be measured (estriol-16α-glucuronide). For this purpose, results of the cross-reactivity test of antibodies are used as a reference.

For example, if an antibody prepared by using an immunogen comprising an estriol-16,17-derivative and an immunoactive carrier bound to the derivative is used, a labelled estrogen corresponding to the antibody may preferably be prepared using an estrone-17-derivative. Naturally, this combination of the antibody and the labelled estrogen is in no way to be taken as limiting.

The following describes the preparation and combination of antibodies and labelled haptens wherein the substance to be measured is blood estradiol.

Measurement of blood estradiol is applied to a monitor system of the female gonadal functions, especially maturation of ovarian follicles and ovulation.

The antibody for use in the measurement of estradiol may be obtained by immunizing an animal with an immunogen which comprises an estradiol-3, 6, 7, 11 or 16-derivative and an immunoactive carrier bound to the derivative and then preparing a hybridoma which produces an anti-estradiol antibody by means of a cell fusion technique.

An antibody prepared by using an immunogen which comprises an estradiol-3 or 6-derivative and an immunoactive carrier bound to the derivative is advantageous in view of the cross-reactivity.

Antibodies thus prepared are then checked for their measurable ranges of estradiol and cross-reactivities to each of the steroids and their derivatives, in order to select an antibody which shows about 200 pg/ml of the 50%-inhibition concentration of estradiol, estimated from a standard curve, and has small cross-reactivities to other steroids than estradiol.

When an antibody for use in the measurement of blood estradiol is prepared by using an immunogen comprising an estradiol-6-derivative and an immunoactive carrier bound to the derivative, a labelled estradiol corresponding to the antibody may preferably be prepared using an estradiol-3-derivative or even the same estradiol-6-derivative provided that the derivatives has a different bridge structure. Naturally, this combination of the antibody and the labelled estradiol is in no way to be taken as limiting.

The following describes the preparation and combination of antibodies and labelled haptens wherein the substance to be measured is blood progesterone.

For the measurement of blood progesterone, it is preferred that the immunoassay reagent or the immunoassay device of the present invention comprises (a) a labelled hapten comprising a first hapten and a labelling agent bound to the first hapten and (b) an antibody prepared by using an immunogen comprising a second hapten and an immunoactive carrier bound to the second hapten, wherein the first and second haptens are individually selected from the group consisting of compounds represented by the formula V:

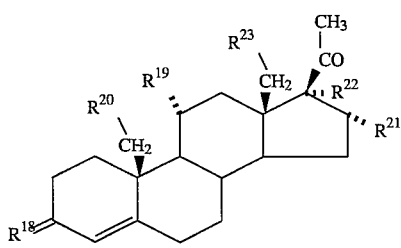

wherein $R^{18}$ is oxygen, one of $R^{19}$, $R^{20}$, $R^{21}$, $R^{22}$ and $R^{23}$ is $Y^5$—Z, and others are hydrogen; or $R^{18}$ is $Y^1$—Z and $R^{19}$, $R^{20}$, $R^{21}$, $R^{22}$ and $R^{23}$ are hydrogen; wherein $Y^1$ is a straight-chain, branched, or cyclic radical intervening Z and the steroid nucleus comprising a backbone having 1 to 10 carbon atoms and/or hereto atoms, bonded to the steroid nucleus by a double bond, $Y^5$ is a straight-chain, branched, or cyclic radical intervening Z and the steroid nucleus or the methylene radical bonded to the steroid nucleus comprising a backbone having 1 to 10 carbon atoms and/or hereto atoms, bonded to the steroid nucleus or the methylene radical bonded to the steroid nucleus by a single bond, and Z is a radical selected from the group consisting of hydrogen, —NH$_2$, —SH, —COOH, —CHO and

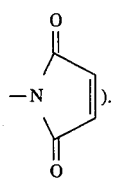

The compound represented by the formula V includes progesterone, progesterone-3-carboxymethyl oxime, progesterone-11α-hemisuccinate, progesterone-16α-hemisuccinate, progesterone-17α-hemisuccinate, progesterone-18-hemisuccinate and progesterone-19-hemisuccinate.

The following describes preparation methods and combinations of antibodies and labelled haptens for use in the immunoassay reagent and the immunoassay device of the present invention for measuring blood progesterone.

Measurement of blood progesterone is applied to the diagnosis of women's gonadal functions, especially luteal function.

The antibody for use in the measurement of progesterone may be obtained by immunizing an animal with an immunogen which comprises a progesterone-3, 11, 16, 17, 18 or 19-derivative and an immunoactive carrier bound to the derivative and then preparing a hybridoma which produces an anti-progesterone antibody by means of a cell fusion technique.

An antibody prepared by using an immunogen which comprises an progesterone-11-derivative and an immunoactive carrier bound to the derivative is advantageous in view of the cross-reactivity.

Antibodies thus prepared are then checked for their measurable ranges of progesterone and cross-reactivities to each of the steroids and their derivatives, in order to select an antibody which shows about 3 ng/ml of the 50%-inhibition concentration of progesterone, estimated from a standard curve, and has small cross-reactivities to steroids other than progesterone.

When an antibody for use in the measurement of blood progesterone is prepared by using an immunogen comprising an progesterone-11-derivative and an immunoactive carrier bound to the derivative, a labelled progesterone corresponding to the antibody may preferably be prepared using a progesterone-19-derivative. Naturally, this combination of the antibody and the labelled progesterone is in no way to be taken as limiting.

Any one of bovine serum albumin, keyhole limpet hemocyanin, Thyroglobulin and the like may be used as an immunoactive carrier in an immunogen for use in the preparation of an antibody which is prepared by using the immunogen comprising a second hapten and the immunoactive carrier bound to the second hapten. Binding of an immunoactive carrier to a hapten may be performed in accordance with any known method described in textbooks and the like, such as Koso Men-eki Sokuteiho [(Enzyme Immunoassay, written in Japanese); published by Igaku Shoin Co., Ltd.; p. 46–60] and Zoku Rajio imuno assei [(Radioimmunoassay, second series; written in Japanese); published by Kodansha Co., Ltd.; p. 56–62 and P. 78–87].

Either monoclonal or polyclonal antibodies may be useful as the antibody of the present invention, but, if a polyclonal antibody is used, it is preferable that the polyclonal antibody be purified into a fraction suitable for the measuring purpose by means of affinity chromatography or the like. Therefore, monoclonal antibodies are preferable as the antibody of the present invention from a workability point of view. Animals for the preparation of antibodies are not limited, but mice are generally used.

With regard to the labelling agent, any of the commonly used agents, such as enzymes including horseradish peroxidase and alkaline phosphatase, radioisotopes including $^{125}$I, fluorescent materials including fluorescein, a fluorescein derivative and europium, and chemiluminescent materials including an acridinium derivative, may be used, preferably an enzyme from the viewpoint of easy handling.

Binding of the labelling agent to a hapten, an antigen or an antibody may be performed in accordance with any known method described in textbooks and the like, such as Koso Men-eki Sokuteiho [(Enzyme Immunoassay, written in Japanese); published by Igaku Shoin Co., Ltd.; p. 46–60].

The immunoassay device of the present invention, wherein the immunoassay reagent of the present invention (a combination of a labelled hapten and an antibody, a labelled antigen and an antibody, a hapten and a labelled antibody or an antigen and a labelled antibody) is included in a container made of a plastic material, a glass material or the like, is produced as follows.

Firstly, an antibody, a hapten or an antigen to be insolubilized is included in a container and insolubilized by means of chemical covalent bonding or physical adsorption. To this is added a portion of a buffer solution containing a corresponding labelled hapten, labelled antigen or labelled antibody, and the mixture is then incubated for a period a time which is sufficient for the completion or near-completion of attaining the equilibrium state of the immune reaction. Thereafter, the contents in the container are subjected to freezing or freeze-drying.

The measuring process is started by the injection of a sample into the container thus prepared. After a certain period of incubation of the sample-added container (a time which is sufficient for attaining completion or near-completion of the equilibrium state of the immune reaction), a B/F separation is performed, and the amount of the substance to be measured in the sample is calculated on the basis of a signal (activity or physical value) originating from the remained labelled material after the B/F separation. The presence of the substance to be detected can be judged in the same manner.

The labelled hapten or the labelled antigen (or the labelled antibody) and the corresponding antibody (or hapten or antigen) in the reagent of the present invention are capable of undergoing reversible binding. When a sample is added to the reagent, therefore, a part of the labelled hapten or labelled antigen (or labelled antibody) once bound to its corresponding antibody (or hapten or antigen) is unbound again in proportion to the amount of a substance to be measured in the sample and, instead, the substance to be measured in the sample is bound to its corresponding antibody, hapten or antigen. In consequence, in spite of the previous binding of the labelled substance to its corresponding antibody, hapten or antigen an by immune reaction, a competitive binding reaction starts between the labelled substance and a substance to be measured when the sample is added to the reagent afterward and the reaction reaches a certain equilibrium state, thus rendering possible development of the competitive binding immunoassay system of the present invention.

When the immunoassay reagent or the immunoassay device of the present invention is used, the equilibrium state of the immune reaction can be obtained quickly within about 30 minutes.

EXAMPLES

Examples of the present invention are given below by way of illustration, and not by way of limitation.

Example 1

Preparation of estradiol-17epi-hemisuccinate, estriol-16, 17-dihemisuccinate, estriol-16epi, 17-dihemisuccinate, progesterone-19-hemisuccinate, progesterone-16α-hemisuccinate, progesterone-17α-hemisuccinate and progesterone-18-hemisuccinate.

Each of 17epi-estradiol, estriol, 16epi-estriol, 19-hydroxy progesterone, 16α-hydroxy progesterone, 17α-hydroxy progesterone, and 18-hydroxy progesterone (all purchased from Sigma Chemical Co.) was dissolved in pyridine, mixed with succinic anhydride (10 to 30 times as much as the starting material on molar basis), and then subjected to heating reflux under nitrogen atmosphere. After cooling the resulting reaction mixture by adding an appropriate amount of water, the water phase was neutralized with dilute hydrochloric acid, and the product was extracted from the water phase by ethyl acetate. The resulting ethyl acetate phase was washed with dilute hydrochloric acid, water, and saturated sodium chloride solution, in that order.

For the isolation of estrogen derivatives, the acid fraction was extracted and separated from the ethyl acetate phase using a saturated sodium carbonate solution. To the acid fraction cooled in an ice bath was added dilute hydrochloric acid in order to acidify the aqueous solution, and the product was extracted by ethyl acetate. The ethyl acetate phase was washed with water and saturated sodium chloride solution, in that order.

Anhydrous sodium sulfate was added to the ethyl acetate solution. After drying the mixture, ethyl acetate remaining in the dried material was evaporated under reduced pressure. Each steroid derivative thus obtained was checked for its purity by thin layer chromatography, and stored for later use. When contamination of the starting material was found by thin layer chromatography, the product was further separated and purified by silica gel column chromatography.

Conditions for the synthesis of each derivative and its yield are shown in Table 1.

TABLE 1

|  | Succinic anhydride (molar ratio) | Reflux time (hr) | Yield (%) |
| --- | --- | --- | --- |
| Estradiol-17epi-hemisuccinate | 20 | 18 | 3 |
| Estriol-16,17-dihemisuccinate | 30 | 20 | 30 |
| Estriol-16epi,17-dihemisuccinate | 30 | 15 | 5 |
| Progesterone-19-hemisuccinate | 10 | 3 | 80 |
| Progesterone-16α-hemisuccinate | 10 | 5 | 60 |
| Progesterone-17α-hemisuccinate | 10 | 3 | 55 |
| Progesterone-18-hemisuccinate | 10 | 3 | 60 |

Example 2

Preparation of estrone-17-carboxymethyl oxime.bovine serum albumin, estradiol-17-hemisuccinate.bovine serum albumin, estriol-16,17-dihemisuccinate.bovine serum albumin, estriol-16α-glucuronide.bovine serum albumin, estradiol-3-carboxymethyl ether.bovine serum albumin, estradiol-6-carboxymethyl oxime.bovine serum albumin, estradiol-6α-hemisuccinate.bovine serum albumin, progesterone-11α-hemisuccinate.bovine serum albumin, progesterone-19-hemisuccinate.bovine serum albumin, progesterone-16α-hemisuccinate.bovine serum albumin, progesterone-17α-hemisuccinate.bovine serum albumin, progesterone-18-hemisuccinate.bovine serum albumin, and progesterone-3-carboxymethyl oxime.bovine serum albumin.

Bovine serum albumin was bound to each of the steroid derivatives listed below by means of a mixed acid anhydride method:

Steroid derivatives prepared in Example 1 consisting of estriol-16,17-dihemisuccinate, progesterone-19-hemisuccinate, progesterone-16α-hemisuccinate, progesterone-17α- hemisuccinate and progesterone-18-hemisuccinate; steroid derivatives purchased from Sigma Chemical Co. consisting of estrone-17-carboxymethyl oxime, estradiol-17-hemisuccinate, estriol-16α-glucuronide, estradiol-6-carboxymethyl oxime, progesterone-11α-hemisuccinate and progesterone-3-carboxymethyl oxime; and steroid derivatives purchased from Mitani Sangyo Co., Ltd. consisting of estradiol-3-carboxymethyl ether and estradiol-6α-hemisuccinate.

The mixed acid anhydride of each steroid derivative was prepared by dissolving each steroid derivative in dioxane and incubating the solution at 12°±2° C. for 20 minutes with gradual dripping of chloroisobutyl formate (equivalent amount to the steroid derivative on a molar basis) in the presence of tri-n-butylamine (molar ratio to the derivative, 1.1).

The mixed acid anhydride of each steroid derivative thus obtained was immediately bound to bovine serum albumin in the following manner. Bovine serum albumin was dissolved in a 50% aqueous solution of dioxane to a final concentration of 10 mg/ml, and the albumin solution was adjusted to pH 8. After cooling down the albumin solution to 10°±2° C., the mixed acid anhydride of each steroid derivative previously prepared was dripped into the albumin solution, with the molar ratio of the anhydride to the bovine serum albumin being 5 to 100. After completion of the dripping, the resulting solution was adjusted to pH 8 and stirred for another 2 hours at 10°±2° C. Thereafter, the reaction solution was transferred into a semi-permeable membrane tube and dialyzed against 100 volumes of physiological saline. The dialysis process was repeated three times and then the product was purified by means of Sephadex G-50 column chromatography.

Example 3

Preparation of estrone-17-carboxymethyl oxime.peroxidase, estradiol-17-hemisuccinate.peroxidase, estriol-16,17-dihemisuccinate.peroxidase, estriol-16α-glucuronide.peroxidase, estradiol-17epi hemisuccinate.peroxidase, estriol-16epi, 17-dihemisuccinate.peroxidase, estradiol-3-carboxymethyl ether.peroxidase, estradiol-6-carboxymethyl oxime.peroxidase, estradiol-6α-hemisuccinate.peroxidase, progesterone-11α-hemisuccinate.peroxidase, progesterone-19-hemisuccinate.peroxidase, progesterone-16α-hemisuccinate.peroxidase and progesterone-3-carboxymethyl oxime.peroxidase.

Horseradish peroxidase was purchased from Toyobo Co., Ltd. and bound to each of the steroid derivatives listed below by means of a mixed acid anhydride method or an N-hydroxysuccinimide ester activation method:

Steroid derivatives purchased from Sigma Chemical Co. consisting of estrone-17-carboxymethyl oxime, estradiol-17-hemisuccinate, estriol-16α-glucuronide, estradiol-6-carboxymethyl oxime, progesterone-11α-hemisuccinate and progesterone-3-carboxymethyl oxime; steroid derivatives purchased from Mitani Sangyo Co., Ltd. consisting of estradiol-3-carboxymethyl ether and estradiol-6α-hemisuccinate; and steroid derivatives prepared in Example 1 consisting of estriol-16,17-dihemisuccinate, estradiol-17epi-hemisuccinate, estriol-16epi,17-dihemisuccinate, progesterone-19-hemisuccinate and progesterone-16α-hemisuccinate.

(3-1) Mixed acid anhydride method.

The mixed acid anhydride of each steroid derivative was prepared by dissolving each steroid derivative in dioxane and incubating the solution at 12°±2° C. for 20 minutes with gradual dripping of chloroisobutyl formate (equivalent amount to the steroid derivative on a molar basis) in the presence of tri-n-butylamine (molar ratio to the derivative, 1.1).

The mixed acid anhydride of each steroid derivative thus obtained was immediately bound to horseradish peroxidase in the following manner. Horseradish peroxidase was dissolved in a 50% aqueous solution of dioxane to its final concentration of 5 mg/ml, and the horseradish peroxidase solution was adjusted to pH 8. After cooling down the peroxidase solution to 10°±2° C., the mixed acid anhydride of each steroid derivative previously prepared was dripped into the peroxidase solution, with molar ratio of the anhydride to the horseradish peroxidase being 1 to 100. After completion of the dripping, the resulting solution was adjusted to pH 8 and stirred for another 2 hours at 10°±2° C. Thereafter, the reaction solution was transferred into a semi-permeable membrane tube and dialyzed against 100 volumes of 0.076M phosphate buffered saline (pH 7.0). The dialysis process was repeated three times and then the product was purified by means of Sephadex G-50 column chromatography.

(3-2) N-hydroxysuccinimide ester activation method.

Each steroid derivative was dissolved in a 95% dioxane aqueous solution, and the resulting solution was mixed with N-hydroxysuccinimide (molar ratio to the steroid derivative, 1.5) and water-soluble carbodiimide (molar ratio, 2) and stirred for 1 to 6 hours. Ethyl acetate was added to the resulting reaction solution and the product was extracted from the water phase by an ethyl acetate phase. The ethyl acetate phase was washed with water and saturated sodium chloride, solution in that order.

Anhydrous sodium sulfate was added to the ethyl acetate solution. After drying the mixture, ethyl acetate remaining in the dried material was evaporated under reduced pressure. The activated steroid derivative thus obtained was dissolved in dioxane and stored at 0° C. or below.

Horseradish peroxidase was dissolved in 50 mM phosphate buffer solution (pH 7.6) to its final concentration of 10 mg/ml. After cooling down the peroxidase solution to 4°±2° C., the activated steroid derivative previously prepared was dripped into the peroxidase solution, with the molar ratio of the activated steroid derivative to the horseradish peroxidase being 1 to 50. After completion of the dripping, the resulting solution was stirred for another 4 hours at 4°±2° C. Thereafter, the reaction solution was transferred into a semi-permeable membrane tube and dialyzed against 100 volumes of 0.076M phosphate buffered saline (pH 7.0). The dialysis process was repeated three times and then the product was purified by means of Sephadex G-50 column chromatography.

Conditions for the synthesis of each labelled steroid derivative are shown in Table 2.

TABLE 2

| Peroxidase-labelled steroid derivative | Labelling method* | Molar ratio of steroid |
|---|---|---|
| Estrone-17-carboxymethyl oxime.peroxidase | A | 1 to 10 |
| Estradiol-17-hemisuccinate.peroxidase | A | 1 to 30 |
| Estriol-16,17-dihemisuccinate.peroxidase | A | 1 to 10 |
| Estriol-16α-glucuronide.peroxidase | A | 5 to 50 |
| Estradiol-17epi-hemisuccinate.peroxidase | A | 10 to 100 |
| Estriol-16epi,17-dihemisuccinate.peroxidase | A | 10 to 100 |
| Estradiol-3-carboxymethyl ether.peroxidase | A | 1 to 30 |

TABLE 2-continued

| Peroxidase-labelled steroid derivative | Labelling method* | Molar ratio of steroid |
|---|---|---|
| Estradiol-6-carboxymethyl oxime.peroxidase | A | 1 to 30 |
| Estradiol-6α-hemisuccinate.peroxidase | B | 1 to 10 |
| Progesterone-11α-hemisuccinate.peroxidase | B | 1 to 10 |
| Progesterone-19-hemisuccinate.peroxidase | B | 1 to 30 |
| Progesterone-16α-hemisuccinate.peroxidase | B | 1 to 50 |
| Progesterone-3-carboxymethyl oxime.peroxidase | A | 1 to 30 |

*:A, Mixed acid anhydride method; and B, N-hydroxysuccinimide ester activation method.

Example 4

Preparation of monoclonal anti-estrogen antibodies.

Balb/c mice were immunized with an immunogen prepared by binding an estrogen derivative to bovine serum albumin. Changes in the blood antibody titer were monitored while boostering was performed, and spleen cells of a mouse in which the antibody titer was increased were used for cell fusion. Cell fusion was performed in accordance with the method described in Methods in Enzymology (vol. 73, p. 3 to 46). Culture supernatants of hybridomas thus obtained were screened for the anti-estrogen antibody, and positive hybridomas were cloned. Antibodies thus selected were further checked for their cross-reactions and measurable ranges of estrogen, in order to eliminate any antibody which was found to be inappropriate for the measuring of urinary estrogen. An appropriate antibody produced in a culture supernatant of a hybridoma thus selected was purified by means of affinity column chromatography using protein A.

The process for the preparation of hybridomas which produce anti-estrogen antibodies is shown in Table 3.

TABLE 3

| Immunogen | No. of immunized mice | No. of cell fusions | No. of antibodies selected |
|---|---|---|---|
| Estrone-17-carboxymethyl oxime. bovine serum albumin | 10 | 2 | 0 |
| Estradiol-17-hemisuccinate. bovine serum albumin | 10 | 8 | 30 |
| Estriol-16,17-dihemisuccinate. bovine serum albumin | 10 | 9 | 65 |
| Estriol-16α-glucuronide. bovine serum albumin | 10 | 1 | 0 |

Example 5

Preparation of reagent for use in the measurement of urinary estrogen.

One of the purified monoclonal anti-estrogen antibodies was immobilized in a glass test tube. A portion of a solution containing one of the estrogen derivatives labelled with horseradish peroxidase was added to the test tube, and the labelled antigen was allowed to react with the insoluble antibody for 60 minutes. A portion of a standard estrogen solution (10, 50, 200 or 1000 ng/ml) was then added to the reaction system and the immune reaction was performed for 20 minutes, followed by a washing process. Thereafter, the enzyme (peroxidase) reaction was performed for 10 minutes in the presence of hydrogen peroxide as the substrate and orthophenylenediamine as the color reagent, and then the absorbance of the colored solution was measured.

The solution containing the peroxidase-labelled estrogen derivative was added to another glass tube in which the purified monoclonal anti-estrogen antibody was immobilized. A standard estrogen solution was added immediately after the addition of the solution of the peroxidase-labelled estrogen derivative. After performing 20 minutes of the immune reaction, the enzyme reaction was performed in the same manner as described above, and the result was compared to that of the above result.

Examples of the results are shown in FIGS. 1a, 1b, 1c and 1d, wherein E15-008 (immunogen, estriol-16,17-dihemisuccinate.bovine serum albumin) or E17-102 (immunogen, estradiol-17-hemisuccinate.bovine serum albumin) was used as the antibody and estrone-17-carboxymethyl oxime.peroxidase or estriol-16,17-dihemisuccinate.peroxidase was used as the labelled estrogen derivative.

It was found that a combination of the antibody E15-008 and the peroxidase-labelled estrone-17-carboxymethyl oxime was appropriate for the measurement of urinary estrogen. Also found that E5-057 (immunogen, estriol-16,17 -dihemisuccinate.bovine serum albumin) and E7-006 (immunogen, estradiol-17-hemisuccinate.bovine serum albumin) were appropriate for the measurement of urinary estrogen (data not shown).

Figure 2:
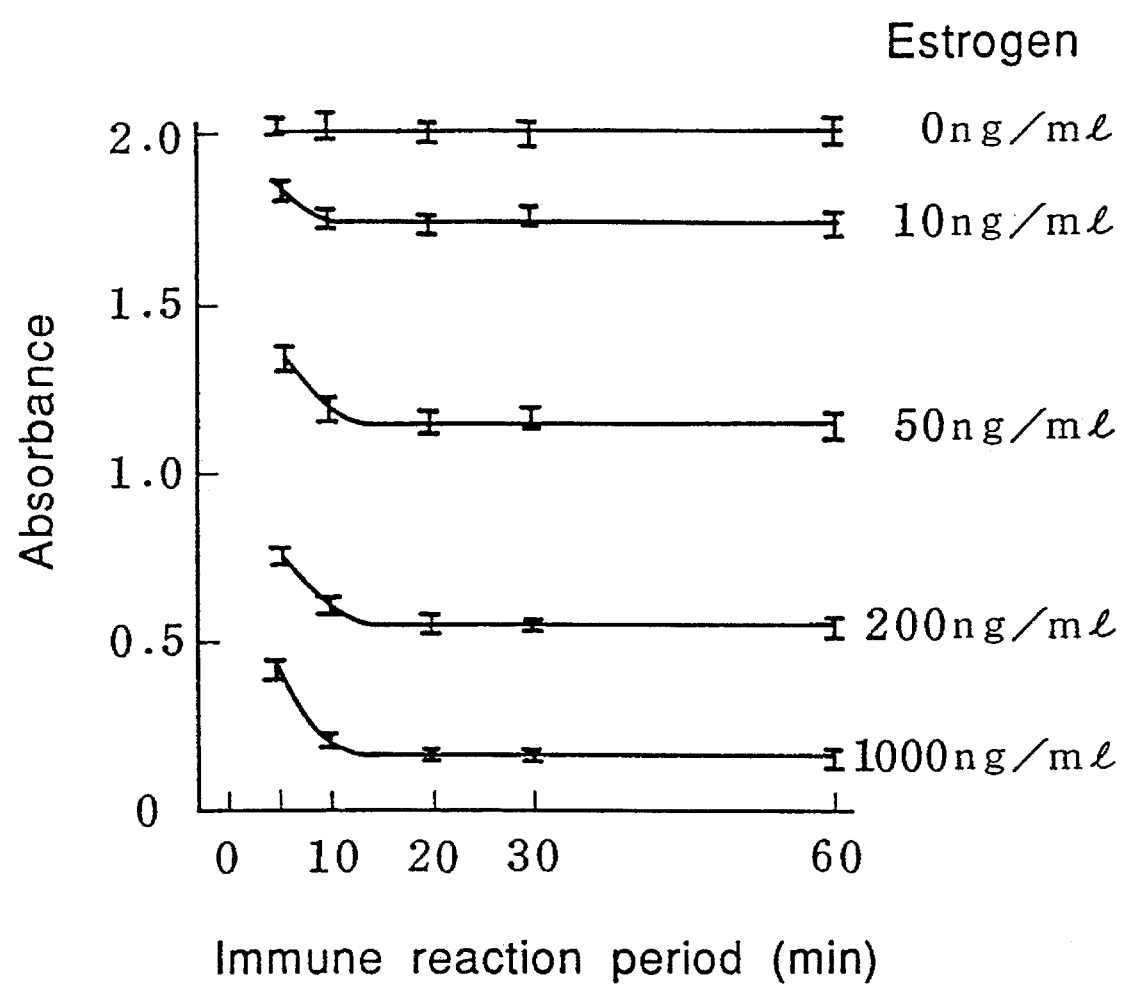
FIG. 2 is a graph showing results of a study on the reaction time required for the completion of equilibrium state in the immune reaction for the measurement of estrogen.
Figure 3A:
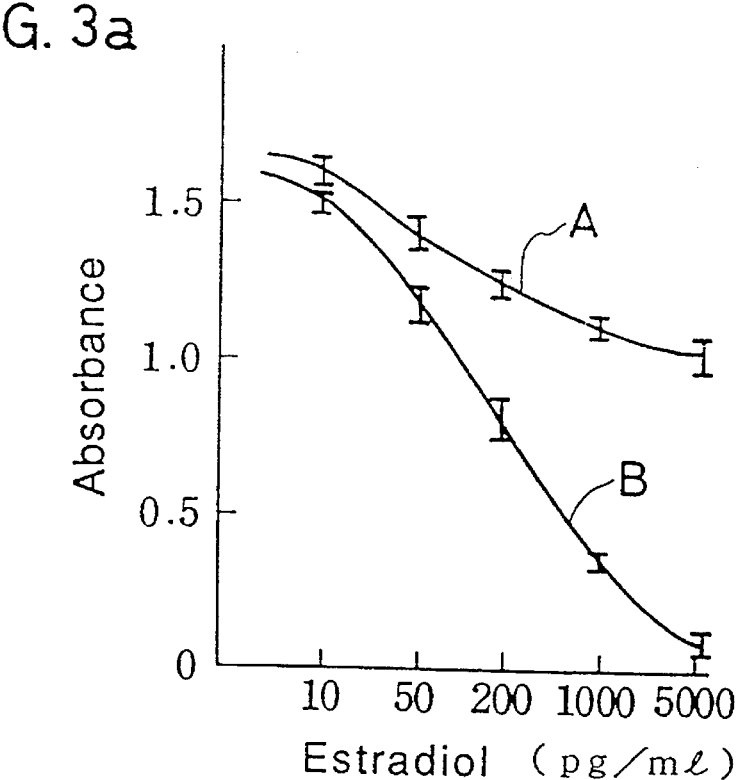
FIGS. 3a, 3b, 3c and 3d are graphs showing results of a study on the existence of reversible immune reaction between anti-estradiol antibodies and labelled estradiol derivatives.
Figure 3B:
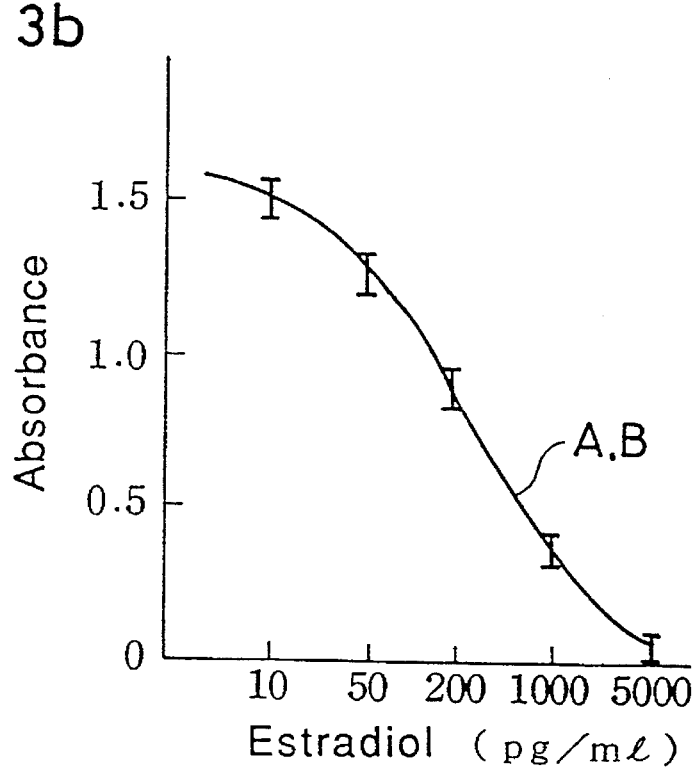
Figure 3C:
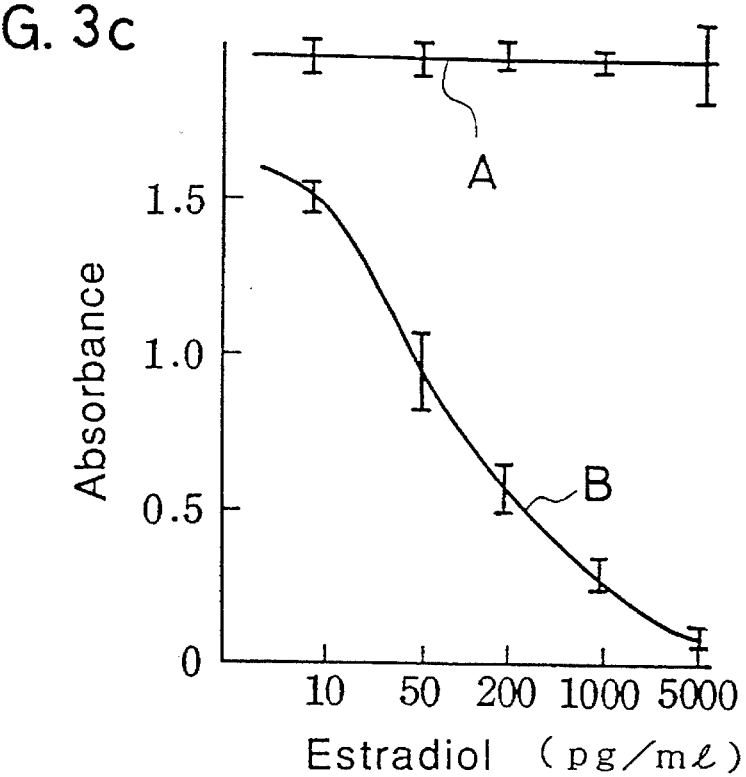
Figure 3D:
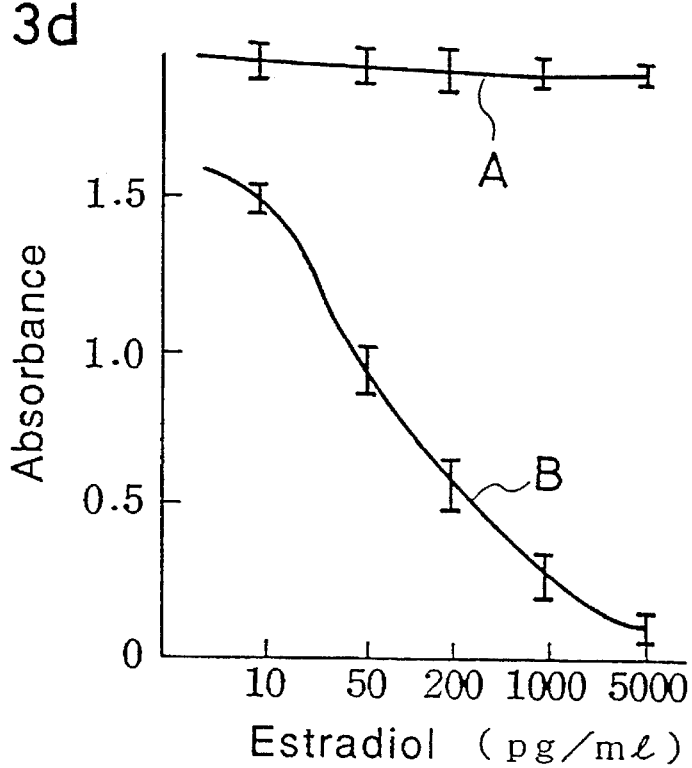
Figure 5A:
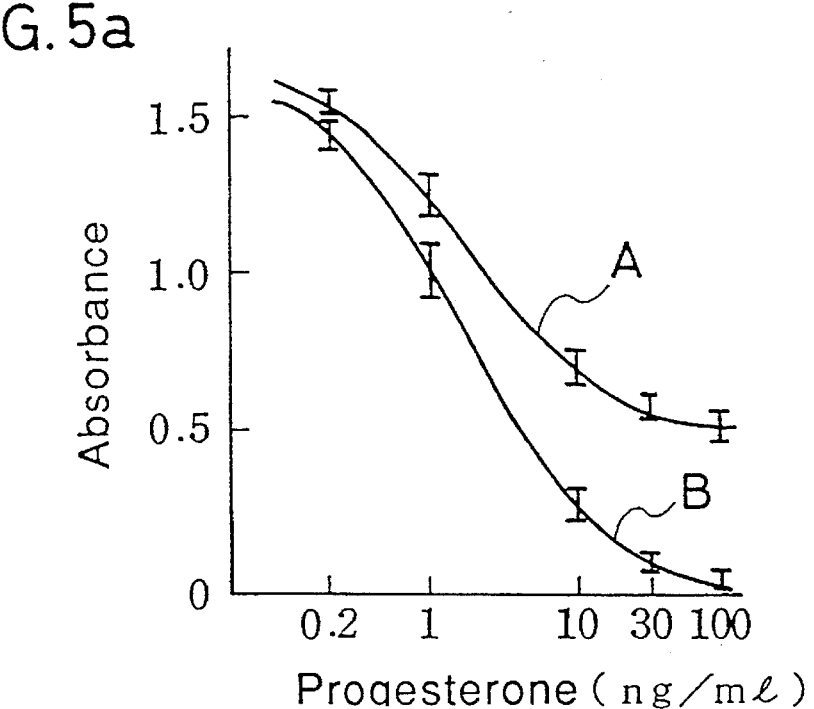
Figure 5B:
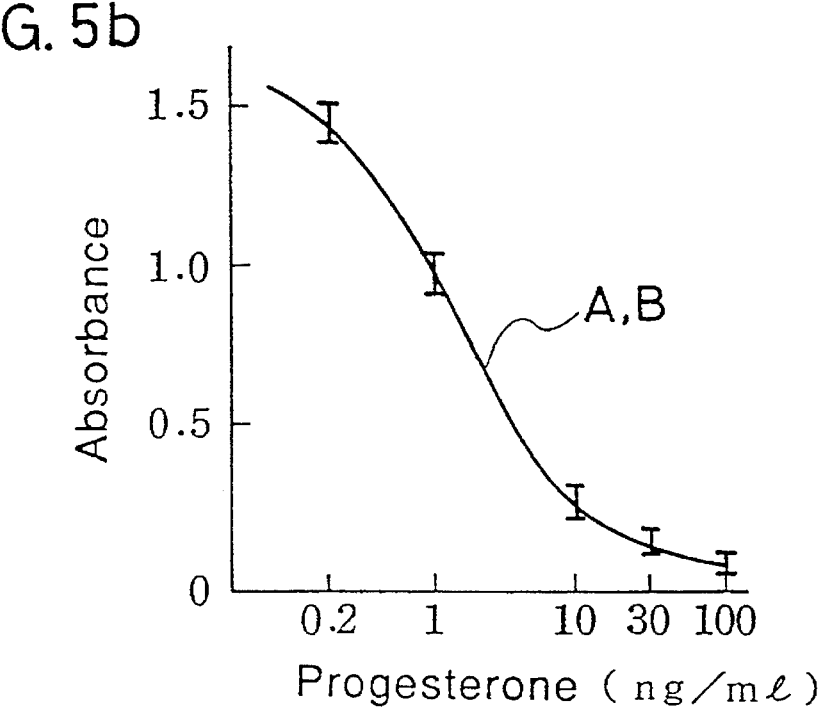

FIG. 2 shows changes in the immune reaction during the reaction period after the addition of a standard estrogen solution, in the case of a combination of the antibody E15-008 and the peroxidase-labelled estrone-17-carboxymethyl oxime.

Based on the result shown in FIG. 2, it was confirmed that the reaction of the antibody with the peroxidase-labelled estrogen is reversible, and the immune reaction, in which the estrogen to be measured in the sample (standard estrogen solution) and the labelled estrogen derivative bind competitively to the antibody, reaches its equilibrium state quickly (about 10 minutes).

Example 6

Preparation of monoclonal anti-estradiol antibodies.

Mice were immunized with an immunogen prepared by binding an estradiol derivative to bovine serum albumin. Changes in the blood antibody titer were monitored while boostering was performed, and spleen cells of a mouse in which the antibody titer was increased were used for cell fusion. Cell fusion was performed in accordance with the method described in Methods in Enzymology (vol. 73, p. 3 to 46). Culture supernatants of hybridomas thus obtained were screened for the anti-estradiol antibody, and positive hybridomas were cloned. Antibodies thus selected were further checked for their cross-reactions and measurable ranges of estradiol, in order to eliminate any antibody which was found to be inappropriate for the measuring of blood estradiol. An appropriate antibody produced in a culture supernatants of a hybridoma thus selected was purified by means of affinity column chromatography using protein A.

The process for the preparation of hybridomas which produce anti-estradiol antibodies is shown in Table 4.

TABLE 4

| Immunogens | Immunized mice | No. of immunized mice | No. of cell fusions | No. of antibodies selected |
| --- | --- | --- | --- | --- |
| Estradiol-3-carboxymethyl ether.bovine serum albumin | Balb/c | 10 | 4 | 0 |
|  | ddY | 10 | 3 | 1 |
| Estradiol-6-carboxymethyl oxime.bovine serum albumin | Balb/c | 30 | 14 | 11 |
|  | ddY | 20 | 11 | 12 |
| Estradiol-6α-hemisuccinate. bovine serum albumin | Balb/c | 30 | 9 | 3 |
|  | ddY | 30 | 14 | 4 |

Example 7

Preparation of reagent for use in the measurement of blood estradiol.

One of the purified monoclonal anti-estradiol antibodies was immobilized in a glass test tube. To this was added a portion of a solution containing one of the estradiol derivatives labelled with horseradish peroxidase, and the labelled antigen was allowed to react with the insoluble antibody for 60 minutes. A portion of a standard estradiol solution (10, 50, 200, 1000 or 5000 pg/ml) was then added to the reaction system and the immune reaction was performed for 20 minutes, followed by a washing process. Thereafter, the enzyme (peroxidase) reaction was performed for 10 minutes in the presence of hydrogen peroxide as the substrate and orthophenylenediamine as the color reagent, and then the absorbance of the colored substance was measured.

To another glass tube in which the purified monoclonal anti-estradiol antibody had been immobilized was added the solution containing the peroxidase-labelled estradiol derivative, followed by the immediate addition of the standard estradiol solution by eliminating the step for the reaction of the insoluble antibody with the labelled antigen. After performing 20 minutes of the immune reaction, the enzyme reaction was performed in the same manner as described above, and the result was compared to that of the above result.

Examples of the results are shown in FIGS. 3a, 3b, 3c and 3d, wherein $E_2$13-074 (immunogen, estradiol-6-carboxymethyl oxime.bovine serum albumin) or $E_2$26-109 (immunogen, estradiol-6-carboxymethyl oxime.bovine serum albumin) was used as the antibody and estradiol-6-carboxymethyl oxime-peroxidase or estradiol-6α-hemisuccinate.peroxidase was used as the labelled estradiol derivative.

It was found that a combination of the antibody $E_2$13-074 and the peroxidase-labelled estradiol-6α-hemisuccinate was appropriate for the measurement of blood estradiol. Antibodies other than the $E_2$13-074 were found to be inappropriate for the measurement of blood estradiol.

FIG. 4 shows changes in the immune reaction during the reaction period after the addition of a standard estradiol solution, in the case of a combination of the antibody $E_2$13-074 and the peroxidase-labelled estradiol-6α-hemisuccinate.

Based on the result as shown in FIG. 4, it was confirmed that the reaction of the antibody with the peroxidase-labelled estradiol is reversible, and the immune reaction, in which the estradiol to be measured in the sample (standard estradiol solution) and the labelled estradiol derivative bind competitively to the antibody, reaches its equilibrium state quickly (about 20 minutes).

Example 8

Preparation of monoclonal anti-progesterone antibodies.

Mice were immunized with an immunogen prepared by binding a progesterone derivative to bovine serum albumin. Changes in the blood antibody titer were monitored while boostering was performed, and spleen cells of a mouse in which the antibody titer was increased were used for cell fusion. The cell fusion was performed in accordance with the method described in Methods in Enzymology (vol. 73, p. 3 to 46). Culture supernatants of hybridomas thus obtained were screened for the anti-progesterone antibody, and positive hybridomas were cloned. Antibodies thus selected were further checked for their cross-reactions and measurable ranges of progesterone, in order to eliminate any antibody which was found to be inappropriate for the measuring of blood progesterone. An appropriate antibody produced in a culture filtrate of a hybridoma thus selected was purified by means of affinity column chromatography using protein A.

The process for the preparation of hybridomas which produce anti-progesterone antibodies is shown in Table 5.

TABLE 5

| Immunogens | Immunized mice | No. of immunized mice | No. of cell fusions | No. of antibodies selected |
| --- | --- | --- | --- | --- |
| Progesterone-11α-hemisuccinate.bovine serum albumin | Balb/c | 10 | 8 | 9 |
|  | ddY | 10 | 3 | 11 |
| Progesterone-19-hemisuccinate.bovine serum albumin | Balb/c | 10 | 4 | 4 |
|  | ddY | 10 | 3 | 2 |
| Progesterone-16α-. hemisuccinate.bovine serum albumin | Balb/c | 10 | 3 | 0 |
|  | ddY | 5 | 2 | 0 |
| Progesterone-3-carboxymethyl oxime. bovine serum albumin | Balb/c | 5 | 1 | 0 |

Example 9

Preparation of a reagent for use in the measurement of blood progesterone.

One of the purified monoclonal anti-progesterone antibodies was immobilized in a glass test tube. To this was added a portion of a solution containing one of the progesterone derivatives labelled with horseradish peroxidase, and the labelled antigen was allowed to react with the insoluble antibody for 60 minutes. A portion of a standard progesterone solution (0.2, 1, 10, 30 or 100 ng/ml) was then added to the reaction system and the immune reaction was performed for 20 minutes, followed by a washing process. Thereafter, the enzyme (peroxidase) reaction was performed for 10 minutes in the presence of hydrogen peroxide as the substrate and orthophenylenediamine as the color reagent, and then the absorbance of the colored substance was measured.

To another glass tube in which the purified monoclonal anti-progesterone antibody had been immobilized was added the solution containing the peroxidase-labelled progesterone derivative, followed by the immediate addition of the standard progesterone solution by eliminating the step for the reaction of the insoluble antibody with the labelled antigen. After performing 20 minutes of the immune reaction, the enzyme reaction was performed in the same manner as described above, and the result was compared to that of the above result.

Examples of the results are shown in FIGS. 5a, 5b, 5c and 5d, wherein P7-006 (immunogen, progesterone-11α-hemisuccinate.bovine serum albumin) or P15-037 (immunogen, progesterone-11α-hemisuccinate.bovine serum albumin) was used as the antibody and progesterone-11α-hemisuccinate.peroxidase or progesterone-19-hemisuccinate.peroxidase was used as the labelled progesterone derivative.

It was found that a combination of the antibody P7-006 and the peroxidase-labelled progesterone-19-hemisuccinate was appropriate for the measurement of blood progesterone. It was found also that P6-057 (immunogen, progesterone-11α-hemisuccinate.bovine serum albumin) and P17-016 (immunogen, progesterone-11α-hemisuccinate.bovine serum albumin) were appropriate for the measurement of blood progesterone (data not shown).

FIG. 6 shows changes in the immune reaction during the reaction period after the addition of a standard progesterone solution, in the case of a combination of the antibody P7-006 and the peroxidase-labelled progesterone-19-hemisuccinate.

Based on the result as shown in FIG. 6, it was confirmed that the reaction of the antibody with the peroxidase-labelled progesterone is reversible and the immune reaction, in which the progesterone to be measured in the sample (standard progesterone solution) and the labelled progesterone derivative bind competitively to the antibody, reaches its equilibrium state quickly (about 20 minutes).

Example 10

Measurement of urinary estrogen.

Antibody E15-008 was immobilized in a glass tube (diameter, 10 mm; length, 65 mm). A 200 μl portion of estrone-17-carboxymethyl oxime.peroxidase solution, with its concentration of 50 ng/ml calculated in terms of peroxidase in the compound, was transferred into the tube and allowed to react with the insoluble antibody. After 60 minutes of the reaction, the resulting solution in the tube was subjected to freeze-drying. The dried body was sealed in the tube against the access of air, and the sealed tube was stored as a device for use in the measurement of urinary estrogen.

Measurement of urinary estrogen was performed as follows. A portion (250 μl under normal conditions) of a sample, which is diluted in advance if necessary, or a standard estrogen solution, was transferred into the above-described device (test tube) for the measurement of urinary estrogen. After 20 minutes of the immune reaction and subsequent washing process, the enzyme (peroxidase) reaction was performed for 10 minutes by adding into the test tube a 500 μl portion of a substrate solution which consisted of orthophenylenediamine (0.3%) as a color reagent and hydrogen peroxide (0.027%) as the substrate. The enzyme reaction was stopped by adding 1000 μl of 3M phosphoric acid solution (sulfuric acid, hydrochloric acid and the like can be used as well), and the absorbance of the colored agent was measured at 492 nm. The concentration of estrogen in the sample was calculated from a standard curve.

The concentration of estrogen in the same sample was separately measured by using commercially available assay kits, and correlation coefficients between the measuring method of the present invention and these commercial kits were calculated. The assay kits used were Radioimmunoassay kit (from Amersham Ltd.), Fluorescence Polarization Immunoassay (from Abbott Lab.) and E₃ Kit (a color reaction system produced by Teikoku Hormone Mfg. Co., Ltd.). A total of 54 samples were checked.

As shown in Table 6, a high correlation was found between the data obtained by using the reagent for immunoassay and the immunoassay device of the present invention and the data obtained by using any of the above-described commonly used measuring methods.

TABLE 6

| Prior art | Correlative relation | Correlation coefficient |
|---|---|---|
| Radioimmunoassay (Amersham) | y = 0.95X − 1.09 | r = 0.96 |
| Fluorescence Polarization Immunoassay (Abbott) | y = 0.86X − 2.39 | r = 0.97 |
| Color reaction (E₃ Kit, Teikoku Hormone Mfg.) | y = 1.12X − 2.74 | r = 0.94 |

Example 11

Measurement of blood estradiol.

Antibody E₂13-074 was immobilized in a glass tube (diameter, 10 mm; length, 65 mm). A 200 μl portion of estradiol-6α-hemisuccinate-peroxidase solution, with its concentration of 10 ng/ml calculated in terms of peroxidase in the compound, was transferred into the tube and allowed to react with the insoluble antibody. After 60 minutes of the reaction, the resulting solution in the tube was subjected to freeze-drying. The dried body was sealed in the tube the access of air, and the sealed tube was stored as a device for use in the measurement of blood estradiol.

Measurement of blood estradiol was performed as follows. A portion (250 μl under normal conditions) of a sample, which is diluted in advance if necessary, or a standard estradiol solution, was transferred into the above-described device (test tube) for the measurement of blood estradiol. After 20 minutes of the immune reaction and subsequent washing process, the enzyme (peroxidase) reaction was performed for 10 minutes by adding into the test tube a 500 μl portion of a substrate solution which consisted of orthophenylenediamine (0.3%) as a color reagent and hydrogen peroxide (0.027%) as the substrate. The enzyme reaction was stopped by adding 1000 μl of 3M phosphoric acid solution (sulfuric acid, hydrochloric acid and the like can be used as well), and the absorbance of the colored solution was measured at 492 nm. The concentration of estradiol in the sample was calculated from a standard curve.

The concentration of estradiol in the same sample was separately measured by using commercially available assay kits, and correlation coefficients between the measuring method of the present invention and these commercial kits were calculated. The assay kits used were Radioimmunoassay (produced by Diagnostic Products Corporation) and Radioimmunoassay (I-125 Kit, produced by Commissariant A Lénegi`e Atomique). A total of 34 samples were checked.

As shown in Table 7, a high correlation was found between the data obtained by using the reagent for immunoassay and the immunoassay device of the present invention and the data obtained by using any of the above-described commonly used measuring methods.

TABLE 7

| Prior art | Correlative relation | Correlation coefficient |
|---|---|---|
| Radioimmunoassay (DPC) | y = 1.13X + 2.12 | r = 0.93 |
| Radioimmunoassay (I-125 Kit, CIS) | y = 1.08X − 3.62 | r = 0.98 |

Example 12

Measurement of blood progesterone.

Antibody P7-006 was immobilized in a glass tube (diameter, 10 mm; length, 65 mm). A 200 µl portion of progesterone-19-hemisuccinate.peroxidase solution, with its concentration of 20 ng/ml calculated in terms of peroxidase in the compound, was transferred into the tube and allowed to react with the insoluble antibody. After 60 minutes of the reaction, resulting solution in the tube was subjected to freeze-drying. The dried body was sealed in the tube against the access of air, and the sealed tube was stored as a device for use in the measurement of blood progesterone.

The measurement of blood progesterone was performed as follows. A portion (250 µl in normal conditions) of a sample, which is diluted in advance if necessary, or a standard progesterone, was transferred into the above-described device (test tube) for the measurement of blood progesterone. After 20 minutes of the immune reaction and subsequent washing process, the enzyme (peroxidase) reaction was performed for 10 minutes by adding into the test tube a 500 µl portion of a substrate solution which consisted of orthophenylenediamine (0.3%) as a color reagent and hydrogen peroxide (0.027%) as the substrate. The enzyme reaction was stopped by adding 1000 µl of 3M phosphoric acid solution (sulfuric acid, hydrochloric acid and the like can be used as well), and the absorbance of the colored solution was measured at 492 nm. The concentration of progesterone in the sample was calculated from a standard curve.

The concentration of progesterone in the same sample was separately measured by using commercially available assay kits, and correlation coefficients between the measuring method of the present invention and these commercial kits were calculated. The assay kits used were Radioimmunoassay (produced by Diagnostic Products Corporation) and Radioimmunoassay (produced by Daiichi Radioisotope Labs., LTD.). A total of 54 samples were checked.

As shown in Table 8, a high correlation was found between the data obtained by using the reagent for immunoassay use and the immunoassay device of the present invention and the data obtained by using any of the above-described commonly used measuring methods.

TABLE 8

| Prior art | Correlative relation | Correlation coefficient |
|---|---|---|
| Radioimmunoassay (DPC) | y = 1.01X − 0.76 | r = 0.93 |
| Radioimmunoassay (Daiichi Radioisotope Labs., LTD.) | y = 1.09X − 0.12 | r = 0.98 |

Thus, it is apparent that there has been provided, in accordance with the present invention, a reagent for use in an immunoassay and an immunoassay device in which the reagent is included in a container, for measuring haptens, antigens or antibodies by means of a competitive binding method.

The immunoassay device of the present invention renders possible easy and simple manual operation and simplification of the mechanical structure of an automatic measuring apparatus, because a process for the supply of a labelled substance is not necessary.

In addition, though the measuring principle according to the present invention is based on the competitive binding method, the reaction are similar to those steps for the sandwich method-based immunoassay. Consequently, by the use of the immunoassay device of the present invention, immunoassay techniques may be carried out more easily, and both the competitive binding method and the sandwich method could be applied to a single automatic measuring apparatus.

While the present invention has been described in conjunction with specific embodiments and examples thereof, it is evident that many alternatives, modifications and variations will be apparent to those skilled in the art in light of the foregoing description. Accordingly, it is intended to include all such alternatives, modifications and variations as set forth within the spirit and scope of the appended claims.

What is claimed is:

1. A reagent for use in an immunoassay for measuring estrogen or estradiol, comprising:

(a) a labelled estrogen or estradiol derivative comprising a first estrogen or estradiol derivative and a labelling agent bound to said first estrogen or estradiol derivative, and (b) an antibody prepared by using an immunogen comprising a second estrogen or estradiol derivative and an immunoactive carrier bound to said second estrogen or estradiol derivative, wherein said first estrogen or estradiol derivative of (a) and said second estrogen or estradiol derivative of (b) are analogous substances that differ from each other in having different chemical structures, respectively, so that said labelled estrogen or estradiol derivative of (a) and said antibody of (b) can undergo reversible binding-unbinding, said labelled estrogen or estradiol derivative of (a) and said antibody of (b) being preliminarily bound before contacting said estrogen or estradiol to be measured and then unbound after contacting said estrogen or estradiol to be measured, facilitating measurement of said estrogen or estradiol to be measured in said immunoassay, and wherein said first and second estrogen or estradiol derivatives are individually selected from the group consisting of compounds represented by formulae I to IV:

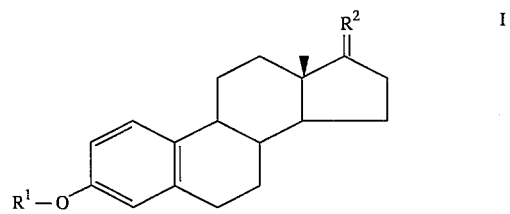

wherein R' is hydrogen and $R^2$ is $Y^1$—Z; or $R^1$ is $Y^2$—Z and $R^2$ is oxygen;

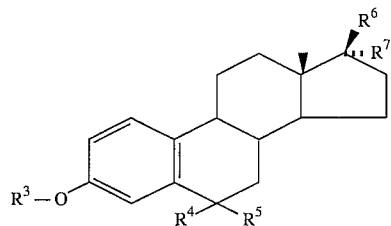

wherein $R^3$, $R^4$ and $R^5$ are hydrogen, one of $R^6$ and $R^7$ is hydrogen, and the other is $Y^3$—Z; $R^3$ is $Y^2$—Z, $R^4$, $R^5$ and $R^7$ are hydrogen, and $R^6$ is $Y^3$—Z; $R^3$ and $R^7$ are hydrogen, one of $R^4$ and $R^5$ is hydrogen and the other is $Y^3$—Z, and $R^6$ is hydroxyl; or $R^3$ and $R^7$ are hydrogen, $R^4$ and $R^5$ together represent $Y^1$—Z bonded to the steroid nucleus by a double bond, and $R^6$ is hydroxyl;

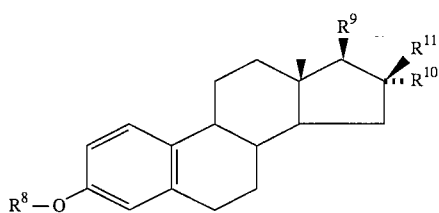

wherein $R^8$ is hydrogen, $R^9$ is $Y^3$—Z and one of $R^{10}$ and $R^{11}$ is $Y^3$—Z, and the other is hydrogen; $R^8$ is hydrogen, one of $R^9$ and $R^{10}$ is hydroxyl and the other is $Y^3$—Z, and $R^{11}$ is hydrogen; or $R^8$ is $Y^2$—Z, $R^9$ is $Y^3$—Z, $R^{10}$ is $Y^4$—Z, and $R^{11}$ is hydrogen; and

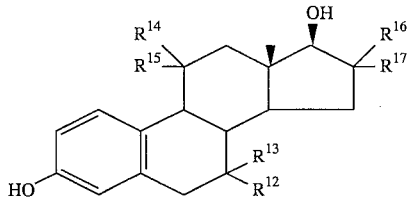

wherein one of $R^{12}$, $R^{13}$, $R^{14}$, $R^{15}$, $R^{16}$ and $R^{17}$ is $Y^3$—Z and the others are hydrogen; or $R^{12}$ and $R^{13}$, $R^{14}$ and $R^{15}$, or $R^{16}$ and $R^{17}$ together represent $Y^1$—Z bonded to the steroid nucleus by a double bond, and the others are hydrogen; wherein $Y^1$ is a straight-chain, branched, or cyclic radical intervening Z and the steroid nucleus comprising a backbone having 1 to 10 carbon atoms and/or hetero atoms, bonded to the steroid nucleus by a double bond; $Y^2$ is a straight-chain, branched, or cyclic radical intervening Z and the oxygen comprising a backbone having 0 to 10 carbon atoms and/or hetero atoms bonded to the oxygen by a single bond; $Y^3$ and $Y^4$ are individually a straight-chain, branched, or cyclic radical intervening Z and the steroid nucleus comprising a backbone having 0 to 10 carbon atoms and/or hetero atoms, bonded to the steroid nucleus by a single bond; and Z is a radical selected from the group consisting of hydrogen, —$NH_2$, —SH, —COOH, —CHO and

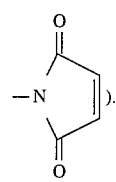

2. A reagent for use in an immunoassay for measuring an estrogen or estradiol according to claim 1, wherein $R^1$, $R^3$ and $R^8$ are hydrogen or $CH_2$—COOH; $R^2$ is oxygen or N—O—$CH_2$—COOH; $R^4$ and $R^5$ are hydrogen, O—CO—$CH_2$—$CH_2$—$CH_2$—COOH, O—CO—$CH_2$—$CH_2$—COOH, O—$CH_2$—COOH, O—$CH_2$—CO—NH—$CH_2$—$CH_2$—$NH_2$ or

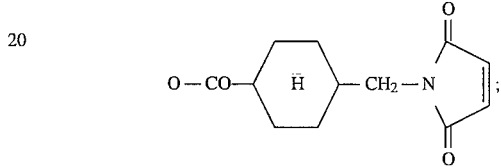

or $R^4$ and $R^5$ taken together represent N—O—$CH_2$—COOH bonded to the steroid nucleus by a double bond; and $R^6$, $R^7$, $R^9$, $R^{10}$ and $R^{11}$ are hydrogen, OH, O—CO—$CH_2$—$CH_2$—COOH, O—CO—$CH_2$—$CH_2$—$CH_2$—COOH or

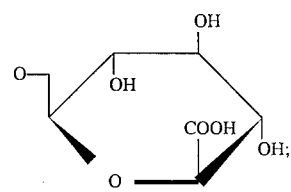

$R^{12}$, $R^{13}$, $R^{14}$, $R^{15}$, $R^{16}$ and $R^{17}$ are hydrogen, O—CO—$CH_2$—$CH_2$—COOH, O—CO—$CH_2$—$CH_2$—$CH_2$—COOH or S—$CH_2$—COOH.

3. A reagent for use in an immunoassay for measuring an estrogen or estradiol according to claim 1, wherein said first and second estrogen or estradiol derivatives are individually selected from the group consisting of estrone, estrone-17-carboxymethyl oxime, estrone-3-carboxymethyl ether, estradiol, estradiol-3-carboxymethyl ether, estradiol-6α-hemisuccinate, estradiol-6-carboxymethyl oxime, estradiol-17α-hemisuccinate and estradiol-17β-hemisuccinate, estriol, estriol-3-carboxymethyl ether, estriol-16α,17β-dihemisuccinate, estriol-16β,17β-dihemisuccinate, estriol-16α-glucuronide, estriol-17β-glucuronide, estradiol-7-hemisuccinate, estradiol-7-carboxyethyl thioether, estradiol-11-hemisuccinate and estradiol-16α-hemisuccinate.

4. A reagent for use in an immunoassay for measuring estrogen or estradiol, comprising:

(c) a first estrogen or estradiol derivative, and (d) a labelled antibody comprising an antibody (b) prepared by using an immunogen comprising a second estrogen or estradiol derivative and an immunoactive carrier bound to said second estrogen or estradiol derivative, and a labelling agent bound to said antibody, wherein said first estrogen or estradiol derivative of (c) and said labelled antibody of (d) can undergo reversible binding, and said first estrogen or estradiol derivative of (c) and said second estrogen or estradiol derivative of (d) of the immunogen used for preparing said antibody (b) of the labelled antibody of (d) are analogous substances that differ from each other in having different chemical structures, respectively, so that said first estrogen or estradiol derivative of (c) and said labelled antibody of (d) can undergo reversible binding-unbinding, said first estrogen or estradiol derivative of (c) and said labelled antibody of (d) being preliminarily bound before contacting said estrogen or estradiol to be measured and then unbound after contacting said estradiol to be measured, facilitating measurement of said estrogen or estradiol to be measured in said immunoassay, wherein said first and second estrogen or estradiol derivatives are individually selected from the group consisting of compounds represented by formulae I to IV:

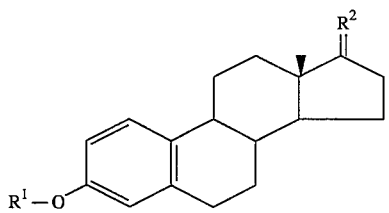

wherein $R^1$ is hydrogen and $R^2$ is $Y^1$—Z; or $R^1$ is $Y^2$—Z and $R^2$ is oxygen;

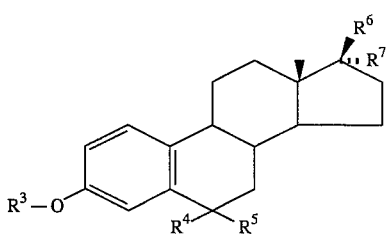

wherein $R^3$, $R^4$ and $R^5$ are hydrogen, one of $R^6$ and $R^7$ is hydrogen, and the other is $Y^3$—Z; $R^3$ is $Y^2$—Z, $R^4$, $R^5$ and $R^7$ are hydrogen, and $R^6$ is $Y^3$—Z; $R^3$ and $R^7$ are hydrogen, one of $R^4$ and $R^5$ is hydrogen and the other is $Y^3$—Z, and $R^6$ is hydroxyl; or $R^3$ and $R^7$ are hydrogen, $R^4$ and $R^5$ together represent $Y^1$—Z bonded to the steroid nucleus by a double bond, and $R^6$ is hydroxyl;

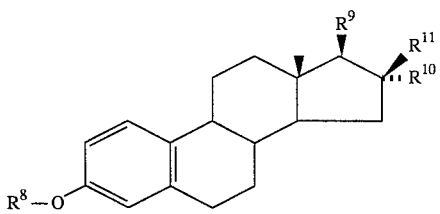

wherein $R^8$ is hydrogen, $R^9$ is $Y^3$—Z and one of $R^{10}$ and $R^{11}$ is $Y^3$—Z, and the other is hydrogen; $R^8$ is hydrogen, one of $R^9$ and $R^{10}$ is hydroxyl and the other is $Y^3$—Z, and $R^{11}$ is hydrogen; or $R^8$ is $Y^2$—Z, $R^9$ is $Y^3$—Z, $R^{10}$ is $Y^4$—Z, and $R^{11}$ is hydrogen; and

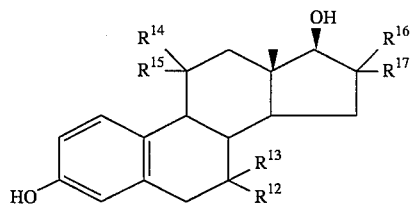

wherein one of $R^{12}$, $R^{13}$, $R^{14}$, $R^{15}$, $R^{16}$ and $R^{17}$ is $Y^3$—Z and the others are hydrogen; or $R^{12}$ and $R^{13}$, $R^{14}$ and $R^{15}$, or $R^{16}$ and $R^{17}$ together represent $Y^1$—Z bonded to the steroid nucleus by a double bond, and the others are hydrogen; wherein $Y^1$ is a straight-chain, branched, or cyclic radical intervening Z and the steroid nucleus comprising a backbone having 1 to 10 carbon atoms and/or hetero atoms, bonded to the steroid nucleus by a double bond; $Y^2$ is a straight-chain, branched, or cyclic radical intervening Z and the oxygen comprising a backbone having 0 to 10 carbon atoms and/or hetero atoms bonded to the oxygen by a single bond; $Y^3$ and $Y^4$ are individually a straight-chain, branched, or cyclic radical intervening Z and the steroid nucleus comprising a backbone having 0 to 10 carbon atoms and/or hetero atoms, bonded to the steroid nucleus by a single bond; and Z is a radical selected from the group consisting of hydrogen, —$NH_2$,— —SH, —COOH, —CHO and

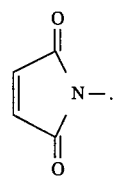

5. A reagent for use in an immunoassay for measuring an estrogen or estradiol according to claim 4, wherein $R^1$, $R^3$ and $R^8$ are hydrogen or $CH_2$—COOH; $R^2$ is oxygen or N—O—$CH_2$—COOH; $R^4$ and $R^5$ are hydrogen, O—CO—$CH_2$—$CH_2$—$CH_2$—COOH, O—CO—$CH_2$—$CH_2$—COOH, O—$CH_2$—COOH, O—$CH_2$—CO—NH—$CH_2$—$CH_2$—$NH_2$ or

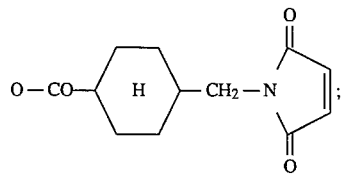

or $R^4$ and $R^5$ taken together represent N—O—$CH_2$—COOH bonded to the steroid nucleus by a double bond; and $R^6$, $R^7$, $R^9$, $R^{10}$ and $R^{11}$ are hydrogen, OH, O—CO—$CH_2$—$CH_2$—COOH, O—CO—$CH_2$—$CH_2$—$CH_2$—COOH or

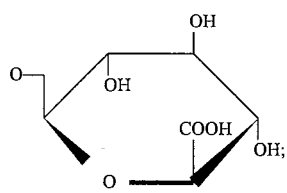

$R^{12}$, $R^{13}$, $R^{14}$, $R^{15}$, $R^{16}$ and $R^{17}$ are hydrogen, O—CO—CH$_2$—CH$_2$—COOH, O—CO—CH$_2$—CH$_2$—CH$_2$—COOH or S—CH$_2$—COOH.

6. A reagent for use in an immunoassay for measuring an estrogen or estradiol according to claim 4, wherein said first and second estrogen or estradiol derivatives are individually selected from the group consisting of estrone, estrone-17-carboxymethyl oxime, estrone-3-carboxymethyl ether, estradiol, estradiol-3-carboxymethyl ether, estradiol-6α-hemisuccinate, estradiol-6-carboxymethyl oxime, estradiol-17α-hemisuccinate and estradiol-17β-hemisuccinate, estriol, estriol-3-carboxymethyl ether, estriol-16α, 17β-dihemisuccinate, estriol-16β, 17β-dihemisuccinate, estriol-16α-glucuronide, estriol-17β-glucuronide, estradiol-7-hemisuccinate, estradiol-7-carboxyethyl thioether, estradiol-11-hemisuccinate and estradiol-16α-hemisuccinate.

7. The reagent for use in an immunoassay for measuring estrogen or estradiol according to claim 1,
wherein said first estrogen or estradiol derivative of (a) and said second estrogen or estradiol derivative of (b) are a combination selected from the group consisting of
(1) a combination of estrone-17-carboxymethyloxime and estriol-16α, 17β-dihemisuccinate,
(2) a combination of estrone-17-carboxymethyloxime and estradiol-17β-hemisuccinate,
(3) a combination of estrone-17-carboxymethyloxime and estriol-16α-glucuronide,
(4) a combination of estriol-16α-glucuronide and estriol-16α, 17β-dihemisuccinate,
(5) a combination of estriol-16α-glucuronide and estradiol-17β-hemisuccinate,
(6) a combination of estradiol-17α-hemisuccinate and estriol-16α, 17β-dihemisuccinate,
(7) a combination of estradiol-17α-hemisuccinate and estradiol-17β-hemisuccinate,
(8) a combination of estradiol-17α-hemisuccinate and estriol-16α-glucuronide, and
(9) a combination of estriol-16β, 17β-dihemisuccinate and estriol-16α, 17β-dihemisuccinate.

8. The reagent for use in an immunoassay for measuring estrogen or estradiol according to claim 1,
wherein said first estrogen or estradiol derivative of (a) and said second estrogen or estradiol derivative of (b) are a combination selected from the group consisting of
(1) a combination of estradiol-6α-hemisuccinate and estradiol-6-carboxymethyloxime,
(2) a combination of estradiol-6α-hemisuccinate and estradiol-3-carboxymethylether,
(3) a combination of estradiol-6-carboxymethyloxime and estradiol-3-carboxymethylether,
(4) a combination of estradiol-6-carboxymethyloxime and estradiol-6α-hemisuccinate,
(5) a combination of estradiol-3-carboxymethylether and estradiol-6-carboxymethyloxime, and
(6) a combination of estradiol-3-carboxymethylether and estradiol-6α-hemisuccinate.

9. The reagent for use in an immunoassay for measuring an estrogen or estradiol according to claim 1,
wherein said first estrogen or estradiol derivative of (a) and said second estrogen or estradiol derivative of (b) are a combination selected from the group consisting of
(1) a combination of estrone-17-carboxymethyloxime and estriol-16α, 17β-dihemisuccinate,
(2) a combination of estrone-17-carboxymethyloxime and estradiol-17β-hemisuccinate,
(3) a combination of estriol-16α-glucuronide and estriol-16α, 17β-dihemisuccinate, and
(4) a combination of estriol-16α-glucuronide and estradiol-17β-hemisuccinate.

10. The reagent for use in an immunoassay for measuring estrogen or estradiol according to claim 1,
wherein said first estrogen or estradiol derivative of (a) and said second estrogen estradiol derivative of (b) are a combination selected from the group consisting of
(1) a combination of estradiol-6α-hemisuccinate and estradiol-6-carboxymethyloxime, and
(2) a combination of estradiol-3-carboxymethylether and estradiol-6-carboxymethyloxime.

11. The reagent for use in an immunoassay for measuring estrogen or estradiol according to claim 4,
wherein said first estrogen or estradiol derivative of (c) and said second estrogen or estradiol derivative of (d) are a combination selected from the group consisting of
(1) a combination of estrone-17-carboxymethyloxime and estriol-16α, 17β-dehemisuccinate,
(2) a combination of estrone-17-carboxymethyloxime and estradiol-17β-hemisuccinate,
(3) a combination of estrone-17-carboxymethyloxime and estriol-16α-glucuronide,
(4) a combination of estriol-16α-glucuronide and estriol-16α, 17β-dihemisuccinate,
(5) a combination of estriol-16α-glucuronide and estradiol-17β-hemisuccinate,
(6) a combination of estradiol-17α-hemisuccinate and estriol-16α, 17β-dihemisuccinate,
(7) a combination of estradiol-17α-hemisuccinate and estradiol-17β-hemisuccinate,
(8) a combination of estradiol-17α-hemisuccinate and estriol-16α-glucuronide, and
(9) a combination of estriol-16β, 17β-dihemisuccinate and estriol-16α, 17β-dihemisuccinate.

12. The reagent for use an immunoassay for measuring estrogen or estradiol according to claim 4,
wherein said first estrogen or estradiol derivative of (c) and said second estrogen or estradiol derivative of (d) are a combination selected from the group consisting of
(1) a combination of estradiol-6α-hemisuccinate and estradiol-6-carboxymethyloxime,
(2) a combination of estradiol-6α-hemisuccinate and estradiol-3-carboxymethylether,
(3) a combination of estradiol-6-carboxymethyloxime and estradiol-3-carboxymethylether,
(4) a combination of estradiol-6-carboxymethyloxime and estradiol-6α-hemisuccinate,
(5) a combination of estradiol-3-carboxymethylether and estradiol-6-carboxymethyloxime, and
(6) a combination of estradiol-3-carboxymethylether and estradiol-6α-hemisuccinate.

13. The reagent for use in an immunoassay for measuring estrogen or estradiol according to claim 4,
wherein said first estrogen or estradiol derivative of (c) and said second estrogen or estradiol derivative of (d) are a combination selected from the group consisting of (1) a combination of estrone-17-carboxymethyloxime and estriol-16α, 17β-dihemisuccinate,
(2) a combination of estrone-17-carboxymethyloxime and estradiol-17β-hemisuccinate,
(3) a combination of estriol-16α-glucuronide and estriol-16α, 17β-dihemisuccinate, and
(4) a combination of estriol-16α-glucuronide and estradiol-17β-hemisuccinate.

14. The reagent for use in an immunoassay for measuring estrogen or estradiol according to claim 4, wherein said first estrogen or estradiol derivative of (c) and said second estrogen or estradiol derivative of (d) are a combination selected from the group consisting of
(1) a combination of estradiol-6α-hemisuccinate and estradiol-6-carboxymethyloxime, and
(2) a combination of estradiol-3-carboxymethylether and estradiol-6-carboxymethyloxime.

* * * * *